(12) United States Patent
Brändli et al.

(10) Patent No.: US 9,945,845 B2
(45) Date of Patent: Apr. 17, 2018

(54) METHODS OF SCREENING USING AMPHIBIANS

(71) Applicants: André W. Brändli, Zollikon (CH); Roland E. Kälin, Berlin (DE)

(72) Inventors: André W. Brändli, Zollikon (CH); Roland E. Kälin, Berlin (DE)

( * ) Notice: Subject to any disclaimer, the term of this patent is extended or adjusted under 35 U.S.C. 154(b) by 0 days.

(21) Appl. No.: 15/803,662

(22) Filed: Nov. 3, 2017

(65) Prior Publication Data

US 2018/0059097 A1 Mar. 1, 2018

Related U.S. Application Data

(63) Continuation of application No. 13/256,209, filed as application No. PCT/EP2010/053613 on Mar. 19, 2010, now abandoned.

(60) Provisional application No. 61/161,497, filed on Mar. 19, 2009.

(51) Int. Cl.
*C12Q 1/68* (2018.01)
*G01N 33/50* (2006.01)

(52) U.S. Cl.
CPC . *G01N 33/5088* (2013.01); *G01N 2333/4606* (2013.01)

(58) Field of Classification Search
None
See application file for complete search history.

(56) References Cited

U.S. PATENT DOCUMENTS

2006/0159676 A1 7/2006 Krieg
2007/0107072 A1 5/2007 Carmeliet

FOREIGN PATENT DOCUMENTS

WO 2006/076736 A2 7/2006

OTHER PUBLICATIONS

Seiffert et al. (2000) J. Biol. Chem. 275:34086-34091.
Kälin et al. (2007) Developmental Biol. 305:599-614.
Kälin et al. (2009) Blood 114:1110-1122.
Gu et al. (1999) Am. J. Physiol. Heart Circ. Physiol. 277:595-602.
Ny et al. (2005) Nature Medicine 11:998-1004.
Wheeler et al. (2009) Developmental Dynamics 238:1287-1308.
Ny et al. (2008) Blood 112:1740-1749.
Tomlinson et al. (2009) Molecular BioSystems 5:376-384.
Tomlinson et al. (2005) Molecular BioSystems 1:223-228.
Feoktistov et al. (2002) Circulation Research 90:531-538.

*Primary Examiner* — Nancy J Leith
(74) *Attorney, Agent, or Firm* — VLP Law Group LLP; David A. Roise

(57) ABSTRACT

High-throughput methods of screening agents for activities affecting renal, cardiac, blood or lymphatic vascular development and functions in amphibians in multiwell plates are provided. Also provided are novel compounds that modulate blood and lymphatic vascular development.

23 Claims, 8 Drawing Sheets

METHODS OF SCREENING USING AMPHIBIANS

CROSS-REFERENCE TO RELATED APPLICATION

This application is a continuation of U.S. patent application Ser. No. 13/256,209, filed on Sep. 12, 2011, which is a national phase application of PCT International Application No. PCT/EP2010/053613, filed Mar. 19, 2010, which claims the benefit of U.S. Provisional Application No. 61/161,497, filed Mar. 19, 2009, the disclosures of which are incorporated herein by reference in their entireties.

FIELD OF THE INVENTION

The present invention provides for in vivo chemical screening methods involving a simple phenotypic read-out (edema formation or lethality), optionally followed by in situ hybridization or immunohistochemistry to screen for agents modulating cardiac, vascular, lymphatic, or renal development or organ functions in amphibian embryos or tadpoles in a multiwell format. Furthermore, active compounds interfering with blood vascular and lymphatic development in *Xenopus laevis* are disclosed. Also provided are screening methods to identify pathways that mediate lymphatic and/or vascular development in an amphibian.

BACKGROUND OF THE INVENTION

Lymphatic vessels play a major role in tissue pressure homeostasis, immune responses, and the uptake of dietary fat and fat-soluble vitamins, as well as in inflammation and cancer progression (Cueni and Detmar, 2006). Recent studies indicate that both lymphatic and blood vessels are involved in chronic inflammatory diseases such as rheumatoid arthritis, inflammatory bowel disease and psoriasis (Alitalo et al., 2005; Carmeliet, 2003; Cueni and Detmar, 2006). But the formation and activation of both types of endothelium have also important roles in the progression and metastasis of the majority of human cancers (Alitalo et al., 2005; Carmeliet, 2003). Tumors need to induce the growth of new blood vessels (angiogenesis) in order to secure the sufficient supply of oxygen and nutrients. The growth of new lymphatic vessels (lymphangiogenesis) has been shown to promote cancer metastasis to sentinel lymph nodes and beyond (Hirakawa et al., 2007; Hirakawa et al., 2005; Mandriota et al., 2001; Skobe et al., 2001; Stacker et al., 2001), a phenomenon which is also found in human neoplasm (Dadras et al., 2005; Tobler and Detmar, 2006). Indeed, studies have revealed that tumor-induced lymphangiogenesis around the primary neoplasm is the most significant prognostic indicator to predict the occurrence of regional lymph node metastasis in human malignant melanomas of the skin (Dadras et al., 2005). More recently, it has been found that tumors can induce lymphangiogenesis in their draining lymph nodes, even before they metastasize and that induction of lymph node lymphangiogenesis promotes the further metastatic cancer spread to distant sites (Hirakawa et al., 2007; Hirakawa et al., 2005). Thus, tumor-induced lymphatic growth and activation represents a promising target for treating or preventing advanced cancer. As a result, there has been a surge of interest in identifying key players that can be used to specifically target these processes therapeutically.

A strong correlation between the expression levels of the lymphangiogenic factor vascular endothelial growth factor-C (VEGFC), tumor lymphangiogenesis and lymph node metastasis has been found in human and in experimental tumors (Pepper et al., 2003). VEGFC promotes lymphangiogenesis by activating VEGF receptor-2 (VEGFR2) and VEGFR3 on lymphatic endothelial cells (Makinen et al., 2001). VEGF-C-deficient mice fail to develop a functional lymphatic system (Karkkainen et al., 2004), and transgenic expression of a soluble VEGFR-3 results in pronounced lymphedema (Makinen et al., 2001). However, blockade of the VEGF-C/VEGFR-3 axis only partially inhibits lymphatic metastasis, indicating that additional pathways are involved in mediating the formation and growth of lymphatic vessels. There have been previous attempts to identify lymphatic specific receptors and pathways by transcriptional and proteomic profiling of cultured lymphatic endothelial cells (LEC) (Hirakawa et al., 2003; Petrova et al., 2002; Roesli et al., 2008). However, large-scale functional in vivo screens to identify molecular pathways or drug-like small molecule modulators of lymphatic vessel formation have been missing to date.

In the last years, cost-efficient maintenance together with abundant experimental techniques and molecular tools, have made zebrafish the only vertebrate model used for large-scale in vivo drug screens (Zon and Peterson, 2005). Amphibians offer many of the same experimental advantages that have favored zebrafish in the past, such as rapid extra-uterine development, the transparency of developing tadpoles, and the permeability of the skin for small molecules, but they have to date not been employed for large-scale chemical library screens to gain insight into vascular development. Amphibians have a common evolutionary history with mammals that is an estimated 100 million years longer than between zebrafish and mammals (Brändli, 2004). Being both tetrapods, amphibians and mammals share extensive synteny at the level of the genomes and have many similarities in organ development, anatomy, and physiology (Christensen et al., 2008; Raciti et al., 2008). These traits favor the use of amphibians for large-scale in vivo drug screens. In the past, embryos and tadpoles of the African clawed frog (*Xenopus laevis*) have served as a powerful animal model to study blood vascular development and angiogenesis (Cleaver and Krieg. 1998; Helbling et al., 2000; Kahn et al., 2007; Levine et al., 2003). More recently, *Xenopus* embryos were shown to develop also a complex, well-defined lymphatic vascular system (Ny et al., 2005). Similar to the development of the mammalian lymphatic vascular system, LECs transdifferentiate from venous blood vascular endothelial cells (BVEC) and lymphangioblasts contribute in *Xenopus* to newly forming lymph vessels that mature to drain fluids from the peripheral tissues back to the blood circulation. Antisense-morpholino knockdown studies of the lymphangiogenic factor VEGFC in *Xenopus* embryos causes lymphatic vessel defects similar to the phenotype observed in VEGFC-deficient mice, including impaired LEC sprouting and migration, and the formation of lymphedema (Karkkainen et al., 2004; Ny et al., 2005).

Various publications have described the use of *Xenopus* embryos in the study of angiogenesis and lymphangiogenesis. For example, U.S. Patent Application Publication No. 2006/0159676 A1 describes methods of inhibiting and promoting various physiological processes, including angiogenesis and lymphangiogenesis by interference with the apelin/APJ signaling pathway, as well as methods of identifying therapeutic agents affecting the apelin/APJ signaling pathway. The reference describes the effects of various treatments on apelin expression in frog embryos, as measured by in situ hybridization, but does not describe an anatomical pattern of edema formation.

U.S. Patent Application Publication No. 2007/0107072 describes transgenic amphibian models for lymphatic vessel development, including assays that allow screening for compounds able to modulate lymphangiogenesis. The reference describes the use of transgenic frog embryos to study the development of the lymphatic vascular network. The reference does not, however, describe an anatomical pattern of edema formation.

There is, therefore, a need for additional methods for in vivo screening in amphibian model systems and for compounds identified using such screens.

SUMMARY OF THE INVENTION

The present invention addresses these problems by providing novel methods for in vivo screening and compounds identified using such methods.

In one aspect, the invention provides a method of screening, comprising the steps of: a) treating a plurality of amphibians with a plurality of agents; b) identifying an amphibian from the plurality of amphibians wherein the treatment causes edema in or death of the amphibian: and c) determining the anatomical pattern of edema formation in the identified amphibian.

In some embodiments, the plurality of amphibians are treated by including the plurality of agents in the culture media containing the plurality of amphibians.

In some embodiments, the plurality of agents are dissolved in the culture media containing the plurality of amphibians.

In some embodiments, the method is performed in a multi-well format.

In some embodiments, the plurality of amphibians are a plurality of embryos, tadpoles, or adults.

In some embodiments, the plurality of amphibians are from the subclass Lissamphibia.

In more specific embodiments, the plurality of amphibians are frogs, toads, newts, salamanders, mudpuppies, or caecilians.

In some embodiments, the plurality of amphibians are from the genus *Xenopus*.

In more specific embodiments, the plurality of amphibians are from the species *Xenopus laevis* or *Xenopus tropicalis*.

In some embodiments, the plurality of agents are independently small molecules, drugs, antibodies, peptides, secreted proteins, nucleic acids, antisense RNA molecules, ribozymes, RNA interference nucleotide sequences, antisense oligomers, or morpholino oligonucleotides.

In some embodiments, the edema or death is caused by an activity in the vascular, lymphatic, cardiac, or excretory system of the identified amphibian.

In some embodiments, the method further comprises the step of identifying the target tissue or organ of the agent responsible for the edema or death in the identified amphibian.

In other embodiments, the anatomical pattern of edema formation in the identified amphibian is cerebral, periocular, pericardial, ventral, proctodeal, pronephric, or tail tip.

In still other embodiments, the anatomical pattern of edema formation in the identified amphibian is a cardiac phenotype or a lymph-heart enlargement.

In some embodiments, the step to identify the amphibian is performed by a secondary screen.

In more specific embodiments, the secondary screen is performed by in situ hybridization or by immunohistochemistry.

In other more specific embodiments, the in situ hybridization is performed manually, semi-automated or fully automated.

In some embodiments, the method further comprises the step of d) identifying the agent causing the edema in or death of the amphibian.

According to another aspect, the invention provides a compound identified by an in vivo screening method comprising the steps of: a) treating a plurality of amphibians with a plurality of agents; b) identifying an amphibian from the plurality of amphibians wherein the treatment causes edema in or death of the amphibian; c) determining the anatomical pattern of edema formation in the identified amphibian; and d) identifying the agent causing the edema in or death of the amphibian.

In more specific embodiments, the methods used to identify the compound are as described above.

In some embodiments of the invention, the compound affects blood vessel development only.

In more specific embodiments of the invention, the compound causes defective vasculogenesis.

In other more specific embodiments, the compound causes defective angiogenesis.

In still other more specific embodiments, the compound causes ectopic angiogenic sprouting.

In still other more specific embodiments, the compound causes vitelline vein network hypoplasia.

In some embodiments of the invention, the compound affects blood and lymph vessel formation.

In more specific embodiments of the invention, the compound causes defective blood and lymph angiogenesis.

In other more specific embodiments, the compound causes vitelline vein network hyperplasia and defective lymph angiogenesis.

In some embodiments of the invention, the compound affects lymph vessel formation only.

In some embodiments of the invention, the compound causes defective lymph angiogenesis.

In another aspect, the invention provides a method for in vivo screening comprising: a) treating a plurality of amphibians with a plurality of agents; b) identifying an amphibian from the plurality of amphibians wherein the treatment causes edema in or death of the amphibian; c) determining the anatomical pattern of edema formation in the identified amphibian; and d) identifying a pathway that mediates lymphatic and/or vascular development in the identified amphibian.

In some embodiments of the invention, the pathway is a VEGF pathway.

In some embodiments of the invention, the pathway is targeted by an adenosine receptor antagonist.

DETAILED DESCRIPTION OF THE INVENTION

Figure 1:
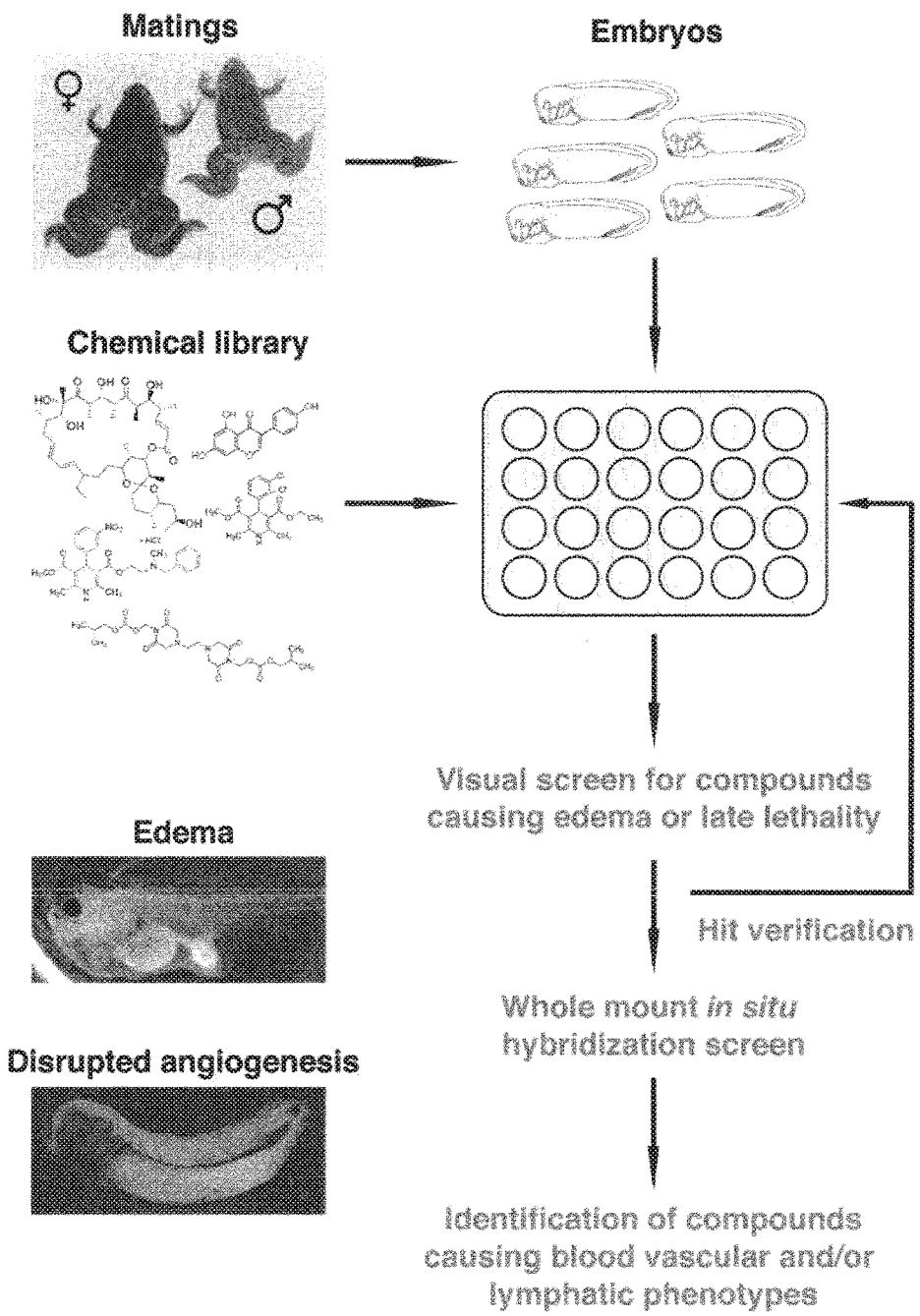
FIG. 1. A chemical library screening method to identify small-molecule modulators of vascular development in *Xenopus* embryos. *Xenopus* embryos were arrayed in multi-well plates and single compounds from the LOPAC[1280] chemical library were added to the water in each well. Embryos were screened visually for developmental defects (edema and/or late lethality). Positive hits are verified by repeating the phenotypic assay. Compounds interfering with vascular development are identified by whole mount in situ hybridization of compound-treated *Xenopus* embryos. Note the screen can also recover compounds affecting cardiac or renal development or function.

Angiogenesis and lymphangiogenesis are essential for organogenesis, but also play important roles in tissue regeneration, chronic inflammation, and tumor progression. Furthermore, defects in the development or function of the cardiovascular and excretory systems underlie major diseases in humans, such as myocardial infarction, stroke, hypertension, and chronic kidney disease. Provided herein are in vivo methods to screen a plurality of agents, such as, for example a chemical library, to identify novel agents and biological mechanisms affecting cardiac, lymphatic, vascular, or renal function in amphibian embryos and tadpoles. In one embodiment of the invention, a novel screening method involving a simple phenotypic read-out (edema formation or lethality) followed by in situ hybridization is used to screen an annotated chemical library of 1,280 bioactive compounds in an multiwell format. In alternative embodiments of the invention, the in situ hybridization step is replaced by immunohistochemical techniques using specific antibodies. Using a two-step screening method of the instant invention, compounds interfering with blood vascular and/or lymphatic development in *Xenopus laevis* are identified. The compounds identified according to the instant screening methods may be used directly in preclinical models of inflammation and cancer metastasis.

The instant invention provides in one aspect an unbiased chemical screening approach in combination with a simple phenotypic readout and in situ hybridization (manual, semi-automated, or fully automated) to identify agents and pathways involved in the development of the cardiac, renal, lymphatic and blood vascular system in *Xenopus* tadpoles.

Also provided according to another aspect of the invention are compounds identified according to the methods of the instant chemical screen. Compounds identified in the screen include compounds affecting vascular and lymphatic development.

In yet another aspect of the invention, novel pathways and targets are identified using the screening methods disclosed herein. Pathways not previously known to mediate lymphatic and/or vascular development are revealed by the screening methods of the invention. In one embodiment, the screening method is used to identify an adenosine A1 receptor antagonist that inhibits lymphatic and blood vessel formation in *Xenopus* tadpoles.

Many of the compounds identified in one of the in vivo screen embodiments of the invention are also active in at least one of four different endothelial in vitro assays, such as cell proliferation and tube formation. Taken together, the various aspects of the instant invention establish rapid and sensitive in vivo methods for large-scale chemical screens using amphibians to identify novel pathways and lead compounds with selectivity for lymphatic and blood vessel formation in a time- and cost-saving manner.

The disclosed screening methods also provide for the identification of and recovery of compounds affecting cardiac and excretory system development and function. The whole-organism based screening methods of the instant invention are more informative than in vitro screening assays and therefore accelerate the development and testing of new drug candidates for the treatment of disorders such as chronic inflammation and cancer.

In one aspect, the invention provides a method for in vivo screening comprising: a) treating a plurality of amphibians with a plurality of agents; b) identifying an amphibian from the plurality of amphibians wherein the treatment causes edema in or death of the amphibian; and c) determining the anatomical pattern of edema formation in the identified amphibian.

According to some embodiments of the invention, the plurality of agents used in the screening methods are small molecules, drugs, antibodies, peptides, secreted proteins, nucleic acids, antisense RNA molecules, ribozymes, RNA interference nucleotide sequences, antisense oligomers, or morpholino oligonucleotides. However, any agent having an effect of interest on the plurality of amphibians could potentially be of interest and use in carrying out the methods of the invention.

In preferred embodiments of the invention, the plurality of agents used in the screening methods are part of a library of agents such as, for example, a chemical or compound library. For purposes of the invention, a chemical library or compound library is a collection of stored chemicals (agent or compound) usually used in low- and high-throughput drug discovery screening procedures. Typically, the chemical library consists of a series of stored chemicals with a specific chemical composition. Each chemical is associated with information stored in some kind of database with information such as the chemical structure, purity, quantity, and physiochemical characteristics of the chemical. In drug discovery screening, such as, for example, in some of the screening methods of the instant invention, it is desirable to screen a drug target or a biological process against a selection of chemicals that represent as much of the appropriate chemical space as possible. The term "drug target" describes the native protein or other biomolecule in the body whose activity is affected by a drug (i.e. chemical, compound, or agent) resulting in a particular biological or therapeutic effect. The targets may include without limitation: G protein coupled receptors, enzymes (such as protein kinases), ligand-gated ion channels, voltage-gated ion channels, solute carriers, nuclear hormone receptors, structural proteins, nucleic acids (including e.g., deoxyribonucleic acids and ribonucleic acids), lipids, lipoproteins, and membranes.

The plurality of agents are used to treat a plurality of amphibians according to the methods of the instant invention. As would be understood by those of ordinary skill in the art, the plurality of agents may be usefully delivered to the plurality of amphibians by any means. For example, in some embodiments of the invention, the plurality of amphibians are treated by including the plurality of agents in the culture media containing the amphibians. In preferred embodiments, the plurality of agents are dissolved in the culture media containing the plurality of amphibians.

It would also be understood by those of ordinary skill in the art that the plurality of amphibians are typically treated independently with the plurality of agents according to the methods of the invention. In other words, individual amphibians are separately treated with individual agents so that specific effects of each agent on an individual amphibian can be determined. It is within the scope of the invention, however, that mixtures of agents could also be used to treat individual amphibians according to the instant methods. Such mixtures may be useful in identifying agents having combinatorial activities on the amphibians in the screening methods. It is also within the scope of the invention that other conditions, such as, e.g., concentration of agent, composition of culture media, temperature, and so on, may also be varied as desired in the practice of the instant methods.

In preferred embodiments of the invention, the plurality of agents are dissolved in the culture media containing the plurality of amphibians. However, other means of treatment of the amphibians by the agents are understood to be within the scope of the invention, as would be apparent to one of ordinary skill in the art.

In some embodiments of the invention, the methods are performed in a multi-well format. As is understood by those of ordinary skill in the art, multi-well format typically refers to a specific arrangement of plastic Petri dishes (also known as culture plates), where two or more dishes are incorporated into one plastic lidded container to create, what is called a multi-well plate. Multi-well plates may typically harbor 6, 12, 24, 48, 96 or 384 wells. The multiwell plate format is designed specifically for high-throughput experiments on a small scale. In the context of the present invention, multi-well format may refer to the use of 12-, 24-, or 48-well plates to culture embryos or tadpoles for the parallel testing and characterization of thousands of chemical agents.

The methods of the instant invention include the step of identifying an amphibian from the plurality of amphibians, wherein the treatment causes edema in or death of the amphibian. In other words, the methods include a procedure or test to identify agents, which may be present in a chemical library, that elicit a desired biological activity. The screen may test agents on whole amphibian organisms to identify agents that elicit a phenotype of interest. A phenotype is defined as any observable characteristic or trait of an organism: such as its morphology, development, biochemical, metabolic or physiological properties, or behavior. The phenotypes are compared with control organisms, which are mock treated or are untreated. The observed phenotype is the result of the agent modulating the expression of the organism's genes, the activity of its gene products (e.g. mRNA, proteins) or other constituents (e.g. lipids, metabolic products). Typically, the screen is simple, fast, and cost-effective. These characteristics permit the rapid selection of agents with desirable bioactivity.

In some embodiments of the invention, the plurality of amphibians are a plurality of embryos, tadpoles, or adults. As used herein, the term "embryo" is defined as a multicellular diploid eukaryote in its earliest stage of development, from the time of first cell division until birth, hatching or germination. The development of a fertilized egg (zygote) into embryo is called embryogenesis. In animals, the development of the zygote into an embryo proceeds through specific recognizable stages of blastula, gastrula, neurula, and organogenesis. In amphibians, fertilized eggs and the resulting multicellular organisms are called by convention embryos from fertilization through hatching, which is defined as the stage when the embryo breaks the covering vitelline membrane. After hatching, the free-swimming amphibian is called a tadpole.

As used herein, the term "tadpole" is defined as the wholly aquatic larval stage in the life cycle of an amphibian, particularly of a frog or toad. Tadpoles are young amphibians that live in the water. During the tadpole stage of the amphibian life cycle, most respire by means of autonomous external or internal gills. Tadpoles do not usually have limbs (arms or legs) until the transition to adulthood.

As used herein, the term "adult" is defined as a biologically grown or mature organism. In amphibians, a tadpole matures into an adult by undergoing metamorphosis, a biological process of transformation, involving a conspicuous and relatively abrupt change in the animal's body structure through cell growth and differentiation. The tadpole metamorphosizes by gradually growing limbs (usually the legs first, followed by the arms) and then outwardly absorbing its tail by apotosis. Lungs develop around the time of leg development. During the final stages of external metamorphosis, the tadpole's mouth changes from a small enclosed mouth at the front of the head to a large mouth the same width as the head. The intestines shorten to make way for the new diet. With the completion of metamorphosis an adult organism emerges, which is usually (but not always) accompanied by a change of habitat usually from water to land.

In some embodiments of the invention, the methods further comprise the step of identifying the target tissue or organ of the agent responsible for the edema or death in the identified amphibian. As used herein, the terms target tissue or organ refer to cellular structures of the organism (e.g. embryo, tadpole or adult) that are affected by the biological or pharmacological activity of an agent, which had been absorbed by the organism. Tissue is in this context considered a cellular organizational level intermediate between cells and a complete organ. Hence, a tissue is an ensemble of cells, not necessarily identical, but from the same origin, that together carry out a specific function. Animal tissues are typically grouped into four basic types: connective tissue, muscle tissue, nervous tissue, and epithelial tissue. The functional grouping and assembly of multiple tissues then form organs. An organ is therefore a collection of tissues joined in a structural unit to serve one or more common physiological functions.

The methods of the instant invention further include the step of determining the anatomical pattern of edema formation in the identified amphibian. As described in detail in the Examples, edema formation in response to compound treatment in an amphibian may be initially highly regionalized, i.e. restricted to a specific organ or tissue, before becoming generalized to the whole body. Hence, according to the methods of the invention, the anatomical distribution and the temporal onset of edemas resulting from the treatment step may be analyzed to determine an anatomical pattern.

In some embodiments of the invention, the anatomical pattern of edema formation in an amphibian identified according to the method is cerebral, periocular, pericardial, ventral, proctodeal, pronephric, or tail tip. In some embodiments of the invention, the anatomical pattern of edema formation is a cardiac phenotype or a lymph-heart enlargement.

In some embodiments of the instant invention, a secondary screen is implemented on the basis of the results obtained in the initial or primary screen. The purpose of this secondary screen is to identify and characterize in greater detail the biological activity of agents recovered in the primary screen. In preferred embodiments of the invention, the secondary screen is performed by in situ hybridization or immunohistochemical procedures. In each procedure, molecular markers (antigens or nucleic acids) are visualized, and changes in their expression are compared to control organisms, which are mock treated or are untreated. Common screenable phenotypes in the secondary screen involve, for example, absent, enhanced, abnormal, and ectopic expression of the molecular marker gene monitored in the secondary screen. Changes in the expression of a marker gene may provide important clues about changes in morphogenesis, tissue formation, organogenesis or homeostasis after the organism was exposed to the agent.

In preferred embodiments of the invention, the step to identify the amphibian is performed by in situ hybridization. In situ hybridization is a type of hybridization procedure that uses a labeled complementary oligonucleotide, deoxyribonucleic acid (cDNA) or ribonucleic acid (RNA) strand typically termed the "probe" to localize a specific DNA or RNA sequence in a portion or section of a tissue in situ (i.e.

in the place). Alternatively, in situ hybridization can be carried out in whole mount on an entire organism, for example if the whole organism is small enough (e.g. embryo, larvae, and tadpole). Hybridization is the process of establishing a non-covalent, sequence-specific interaction between two or more complementary strands of nucleic acids into a single hybrid, which in the case of two strands is referred to as a duplex. Oligonucleotides, DNA, or RNA will bind to their complement under normal conditions, so that two perfectly complementary strands will bind to each other readily. In situ hybridization is distinct from immunohistochemistry, which localizes proteins in tissue, organs, or whole organisms.

In the context of the present invention, oligonucleotide, DNA, or RNA hybridization may be used in some embodiments to measure and localize messenger RNA (mRNAs), microRNA (miRNA) and other gene transcripts in cells of a tissue, organ, or intact organisms. In situ hybridization samples are whole organisms (e.g. embryos, tadpoles, larvae, adults), organs, or tissues or sections thereof. In situ hybridization may be used in the diagnosis of normal as well as abnormal cells such as those found in tissues and organs that have undergone pathological changes due to cancer or other illnesses. The molecular markers (i.e., mRNA molecules) detected by in situ hybridization may reflect the severity or presence of some disease state. In situ hybridization may also be used to understand the distribution and localization of biomarkers (i.e. differentially expressed mRNA molecules) in different parts of a biological sample. Specific biomarkers are characteristic of particular cellular events such as proliferation, differentiation, or cell death (apoptosis). A biomarker or molecular marker may in this context be, for example, an mRNA molecule native to the tissue, organ, or organism whose detection indicates a normal state or a particular disease state (for example, the presence of a mRNA molecule may indicate an inflammation). The biomarker may therefore be used as an indicator of a particular disease state or some other biological state of a tissue, an organ or an organism. In the context of the present invention and not excluding the above-mentioned applications, in situ hybridization may also be used, for example, to demonstrate and characterize the bioactivity of an agent or a combination of agents in intact organisms.

For in situ hybridization, the intact biological sample (tissues, organs, or whole organisms) or sections thereof are typically treated by organic solvents to fix the target RNA transcripts in place and to increase access of the probe. The probe is typically either a labeled complementary oligonucleotide, DNA or RNA (riboprobe). The probe, for example, hybridizes to the target mRNA sequence at elevated temperature, and then the excess probe is washed away (after prior hydrolysis using RNase in the case of (unhybridized, excess RNA probe). As would be understood by those skilled in the art, solution parameters, such as temperature, salt and/or detergent concentration may be manipulated to remove any non-identical interactions (i.e. only exact sequence matches will remain bound). Then, the probe that was labeled with either radio-, fluorescent- or antigen-labeled bases (e.g. digoxigenin, or biotin) is localized and quantitated in the tissue using either autoradiography, fluorescence microscopy, or immunohistochemistry, respectively. In situ hybridization procedures may also involve the use of two or more probes, labeled with radioactivity or the other non-radioactive labels, to simultaneously detect two or more transcripts in section of a tissue or organ, or in the whole organisms (e.g. embryo, larvae, and tadpole). The basic steps of in situ hybridization procedures typically include, for example, permeabilization of the biological specimen (tissue, organ, embryo) with proteinase K to open cell membranes, although the permeabilization step is not always needed for tissue sections or some early-stage embryos. Next, labeled complementary probes are allowed to bind to the target mRNAs by hybridization. Specific hybrids encompassing the probe and the target mRNA are visualized by staining with an antibody, which recognizes a specific antigen (e.g. digoxigenin or biotin) covalently coupled to the probe molecule. The antibody may be radioactively labeled, covalently coupled with a fluorophore or conjugated with an enzyme such as horse radish peroxidase. The enzyme is used to catalyze a color-producing reaction. Other catalytic enzymes such as alkaline phosphatase may be used instead of peroxidases for both direct and indirect staining methods. Alternatively, the antibody may be detected using the fluorescent label (by immunofluorescence), or radioactivity (by autoradiography). Fluorophores may include, without limitation, fluorescein, rhodamine, DyLight Flour or Alexa Fluor. Other detection techniques, such as, for example, luminescence, may also be used in the methods of the invention.

In situ hybridization procedures of use in the instant methods may be carried out manually, semi-automated or fully automated. Manually refers to procedures carried out by solely hand without using specialized equipment (e.g. machines, instruments, or robots). Semi-automated indicates that parts of procedures are done by specialized equipment, but human intervention may be required for one or more steps. Fully automated in situ hybridization procedures use specialized equipment that may be controlled fully or in part by computers.

For purposes of the methods of the instant invention, immunohistochemistry refers to the process of localizing antigens (e.g. proteins, lipids, glycolipids, or glycans) in cells of a tissue, organ, or intact organisms by exploiting the principle of antibodies binding specifically to antigens in biological samples. Immunohistochemical samples are, for example, whole organisms (e.g. embryos, tadpoles, larvae, adults), organs, or tissues or sections thereof. Immunohistochemical staining may be used in the diagnosis of normal as well as abnormal cells such as those found in tissues and organs that had undergone pathological changes due to cancer or other illnesses. The molecular markers (e.g. antigens) detected by immunochemistry may reflect the severity or presence of some disease state. Immunohistochemistry may also be used to understand the distribution and localization of biomarkers (e.g. differentially expressed antigens) in different parts of a biological sample. Specific biomarkers are characteristic of particular cellular events such as proliferation, differentiation, or cell death (apoptosis). A biomarker or molecular marker can be an antigen native to the tissue, organ, or organism whose detection indicates a normal state or a particular disease state (for example, the presence of a protein may indicate an inflammation). The biomarker is therefore used as an indicator of a particular disease state or some other biological state of a tissue, an organ or an organism. In the context of the present invention, and not excluding the above-mentioned applications, immunohistochemistry may also be used to demonstrate the bioactivity of an agent or a combination of agents in intact organisms.

For purposes of the instant invention, the visualization of an antibody-antigen interaction may be accomplished in a number of ways, as would be understood by those of skill in the art. For example, in the most common instance, an antibody is conjugated to an enzyme, such as peroxidase, that can catalyse a color-producing reaction (immunoperoxidase staining). Other catalytic enzymes such as alkaline phosphatase may be used instead of peroxidases for both direct and indirect staining methods. Alternatively, the antibody may be detected using a fluorescent label (immunofluorescence), may be attached to colloidal gold particles for electron microscopy, or may be made radioactive for autoradiography. Fluorophores of use in the instant methods may include, without limitation, fluorescein, rhodamine, DyLight Flour or Alexa Fluor. Other detection techniques, such as, for example, luminescence, may also be used in the methods of the invention.

The antibodies used in the immunohistochemistry of the instant methods may be polyclonal, i.e. raised by normal antibody reactions in animals, such as horses, sheep or rabbits. Polyclonal antibodies (or antisera) are obtained from different B cell resources. They are typically a combination of immunoglobulin molecules secreted against a specific antigen, each identifying a different antigenic determinant (epitope). Alternatively, monoclonal antibodies can be used that have affinity for the same antigen. Monoclonal antibodies are monospecific, because they are made by one type of immune cell, which are all clones of a unique parent B cell.

Two basic strategies are typically used for time immunohistochemical detection of antigens in tissue, organs, or whole organisms: the direct method and the indirect method. In both cases, many antigens may also need an additional step for unmasking. This may be achieved by detergent treatment or sectioning. The direct method is typically a one-step staining method, and normally involves a labeled antibody (e.g. fluorophore or enzyme conjugated antibody) reacting directly with the antigen in the biological sample. The indirect method typically involves an unlabeled primary antibody (first layer), which reacts with the antigen, and a labeled secondary antibody (second layer), which reacts with the primary antibody. The second layer antibody may be conjugated with a fluorescent dye or an enzyme. The secondary antibody may also be biotinylated and coupled with streptavidin-horseradish peroxidase or other streptavidine-enzyme fusion proteins. The enzymes are typically used to catalyze a color-producing reaction. Finally, the antibody may also be radiolabeled and antibody-antigen complexes are detected by radiography. Other detection techniques, such as, for example, luminescence, may also be used in the methods of the invention.

The immunohistochemical procedures of the instant methods may be carried out manually, semi-automated or fully automated. Manually refers to procedures carried out by solely hand without using specialized equipment machines, instruments, or robots). Semi-automated indicates that parts of procedures may be done by specialized equipment, hut human intervention is required for one or more steps. Fully automated immunohistochemical procedures use specialized equipment that may be controlled fully or in part by computers.

In another aspect, the invention provides compounds identified by an in vivo screening method comprising the steps of: a) treating a plurality of amphibians with a plurality of agents; b) identifying an amphibian from the plurality of amphibians wherein the treatment causes edema in or death of the amphibian; c) determining the anatomical pattern of edema formation in the identified amphibian; and d) identifying the agent causing the edema in or death of the amphibian. As described in detail in the Examples, methods of the instant invention have been used to identify compounds causing various phenotypes in treated amphibians.

In some embodiments of the invention, the compound identified by the in vivo screening method affects blood vessel development only. In more specific embodiments, the compound causes defective vasculogenesis. In even more specific embodiments, the compound causes defective angiogenesis, ectopic angiogenic sprouting, or vitelline vein network (VVN) hypoplasia.

In some embodiments of the invention, the compound affects both blood and lymph vessel formation. In specific embodiments, the compound causes defective blood and lymph angiogenesis or vitelline vein network hyperplasia and defective lymph angiogenesis.

In some embodiments of the invention, the compound affects lymph vessel formation only. In specific embodiments, the compound causes defective lymph angiogenesis.

In another aspect, the invention provides methods for in vivo screening comprising: a) treating a plurality of amphibians with a plurality of agents; b) identifying an amphibian from the plurality of amphibians wherein the treatment causes edema in or death of the amphibian; c) determining the anatomical pattern of edema formation in the identified amphibian; and d) identifying a pathway that mediates lymphatic and/or vascular development in the identified amphibian. In some embodiments of the invention, the pathway is a VEGF pathway. In some embodiments of the invention, the pathway is targeted by an adenosine receptor antagonist.

In yet another aspect, the invention provides novel methods according to the following numbered paragraphs:

1. A method for in vivo screening comprising: a) treating a plurality of amphibians with a plurality of agents; b) identifying an amphibian from the plurality of amphibians wherein the treatment causes edema in or death of the amphibian; and c) determining the anatomical pattern of edema formation in the identified amphibian.
2. The method of paragraph 1, wherein the agent is administered to the amphibian by dissolving the agent in the culture media containing the amphibian.
3. The method of paragraph 1, wherein the method is performed in a multi-well format.
4. The method of paragraph 1, wherein the amphibian is an embryo, tadpole, or adult.
5. The method of paragraph 1, wherein the amphibian is from the subclass Lissamphibia.
6. The method of paragraph 5, wherein the amphibian is a frog, toad, newt, salamander, mudpuppy, or caecilian.
7. The method of paragraph 1, wherein the amphibian is from the genus *Xenopus*.
8. The method of paragraph 7, wherein the amphibian is from the species *Xenopus laevis* or *Xenopus tropicalis*.
9. The method of paragraph 1, wherein the agent is a small molecule, a drug, an antibody, a peptide, a secreted protein, a nucleic acid, an antisense RNA molecule, a ribozyme, an RNA interference nucleotide sequence, an antisense oligomer, or a morpholino oligonucleotide.
10. The method of paragraph 1, wherein the edema or death is caused by an activity in the vascular, lymphatic, cardiac, or excretory system of the identified amphibian.
11. The method of paragraph 1, further comprising the step of identifying the target tissue(s) or organ(s) of the agent responsible for the edema or death in the identified amphibian.
12. The method of any one of paragraphs 1-11, wherein the identifying step is performed by a secondary screen.
13. The method of any one of paragraphs 1-12, wherein the identifying step is performed by in situ hybridization.

14. The method of paragraph 13, wherein the in situ hybridization performed manually, semi-automated or fully automated.
15. The method of any one of paragraphs 1-12, wherein the identifying step is performed by immunohistochemistry.
16. The method of paragraph 15, wherein the immunohistochemistry is performed manually, semi-automated or fully automated.

It will be readily apparent to one of ordinary skill in the relevant arts that other suitable modifications and adaptations to the methods and applications described herein may be made without departing from the scope of the invention or any embodiment thereof. Having now described the present invention in detail, the same will be more clearly understood by reference to the following Examples, which are included herewith for purposes of illustration only and are not intended to be limiting of the invention.

EXAMPLES

Pathological neovascularization is associated with many severe and debilitating diseases such as chronic inflammation, diabetic retinopathy, and cancer. Despite of significant advances in antiangiogenic therapies in recent years, studying the mechanisms of blood and lymphatic vessel formation to define novel therapeutic targets and the identification of novel anti(lymph)angiogenic drugs remains highest priority. This is particularly true for lymphangiogenesis, where the mechanistic understanding and the identification of novel drug targets have been hampered by a lack of an appropriate, simple animal model. The recent imaging and molecular characterization of lymphatic vessel systems in Xenopus tadpoles (Ny et al., 2005) and zebrafish (Kuchler et al., 2006; Yaniv et al., 2006) has created new opportunities for studying vascular development as well as for pharmacological screens. Here the inventors describe in vivo chemical screening methods to identify novel bioactive compounds and to define several novel pathways acting during blood vascular development and lymphangiogenesis in Xenopus tadpoles. In addition, the methods are suitable to identify compounds modulating cardiac and renal development or functions in vivo.

Forward chemical genetics uses the screening of annotated libraries of small organic compounds with experimentally-verified biological mechanisms and activities to study biological systems (Stockwell, 2000). This approach circumvents the well-known problems of target identification and lack of mechanistic understanding associated with active compounds recovered from screens using conventional chemical libraries (Root et al., 2003). Forward chemical genetics has therefore become increasingly used in cell cultures to identify signaling pathways involved in cellular functions in vitro (Diamandis et al., 2007, Rickardson et al., 2006; Root et al., 2003), and more recently, whole organisms such as Drosophila, Caenorhabditis elegans, and zebrafish have been used for compound discovery (Chang et al., 2008; Min et al., 2007; Tran et al., 2007). Importantly, chemical genetics using whole animals offers a complementary approach to loss-of-function mutations or knockdowns with siRNA or morpholino oligonucleotides in the analysis of complex biological processes, such as organogenesis.

Figure 2:
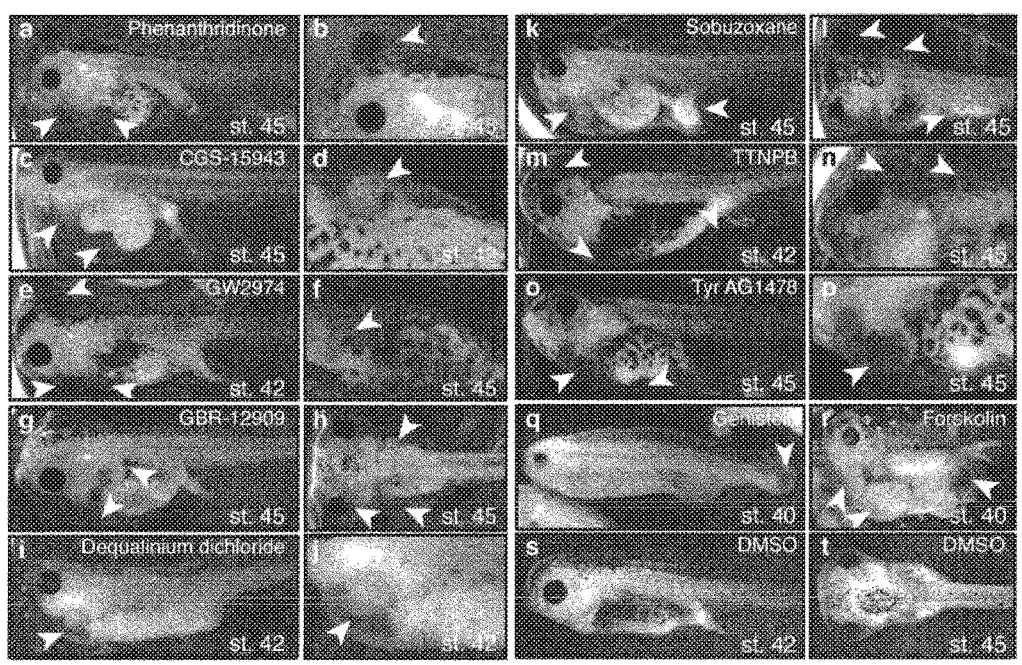
FIG. 2. Distinct edema phenotypes induced by small-molecule compounds in *Xenopus* tadpoles. A selection of compound-treated *Xenopus* tadpoles displaying different classes of edema morphologies is shown (see Table 8 for details): class A (a-f, r); class B (g, h), class C (i, j), class D (k, l), Class E (m, n), and class F (o-q). Pictures of compound-treated (a-r) and control DMSO-treated embryos (s, t) were taken during the screening process at the indicated developmental stages, *Xenopus* tadpoles are generally shown in lateral views. Arrowheads mark primary regions of edema formation. Where required, dorsal views (h, I, t) are shown to highlight particular edema morphologies. Alternatively, magnifications of specific regions such as the head for periocular (b) and cerebral (n) edemas, heart for pericardial edemas (j, p), pronephric kidneys (d) and lymph hearts (f) are shown. Abbreviations: GBR-12909, GBR-12909 dihydrochloride; Phenanthridinone, 6(5H)-Phenanthridinone; Tyr, Tyrphostin.

The use of Xenopus embryos for chemical library screening and drug discovery was previously proposed (Brändli, 2004), and subsequently a small-scale pilot study provided further evidence for the feasibility (Tomlinson et al., 2005), but the phenotypic read-outs useful in the identification of active agents were not understood, nor were phenotypic read-outs combined with secondary screens. The inventors now describe a large-scale two-step chemical screening method in Xenopus embryos to efficiently recover agents affecting vascular, lymphatic, cardiac or renal development and function in vivo (FIG. 1). As utilized herein, the agent or compound can be but is not limited to a chemical, a small molecule, a drug, an antibody, a peptide, a secreted protein, a nucleic acid (such as DNA, RNA, a polynucleotide, an oligonucleotide or a cDNA) or an antisense RNA molecule, a ribozyme, an RNA interference nucleotide sequence, an antisense oligomer or a morpholino oligonucleotides. High-throughput, large-scale screening approaches require a functional phenotypic read-out that is easily detected and reliably predictive for vascular system defects. Edema is the major downstream phenotype caused by impairment of lymphatic vessel development (Ny et al., 2005), but is also associated with disrupted development or function of the cardiovascular and excretory systems in tadpoles (Howland, 1916). The inventors therefore decided to screen the LOPAC$^{1280}$ chemical library by visual inspection for compounds that induce edema. There were several different types/locations of edema induced by different compounds (FIG. 2). Remarkably, compounds targeting the same pathway often revealed similar phenotypes (Table 8). For example, $Ca^{2+}$-channel antagonists induced pericardial and ventral edemas, whereas retinoids caused cerebral and pronephric edemas. Although most gene defects affecting lymphatic vessel development also cause edema formation, the possibility that some compounds might have affected lymphatic (or blood) vessel development without causing edema formation cannot be excluded. The inventors therefore also scored for compounds causing late stage lethality in response to compound treatment. A total of 66 compounds satisfying the screening criteria were recovered with a hit rate of 5%: 48 edema-inducing compounds and 18 compounds causing lethality (Tables 1, 3, and 4). From a practical point of view, the inventors were able to exclude 95% of the compounds as inactive on the basis of a simple, non-invasive phenotypic screening criteria.

Edema formation and lethality may not only be caused by cardiovascular defects, but could also be a consequence of renal dysfunction impairing fluid homeostasis. In the second screening step, compound-treated embryos were therefore subjected to semi-automated whole mount in situ hybridizations using specific blood vascular and lymphatic marker genes. The analysis of vascular marker gene expression revealed that a total of 32 hits (24 of the 48 edema-inducing compounds and 8 of the 18 compounds associated with lethality) caused abnormal vascular development and morphogenesis in tadpoles. The 32 compounds represented 15 distinct pharmacological classes and they could be grouped into three broad vascular phenotype classes on the basis of affecting either blood vascular or lymphatic development only or both (Table 9). Collectively, the phenotypic screening method resulted in recovery of bioactive compounds with an impressive 49.2% hit rate (32 of 65 tested). Alternatively, the second screening step may be performed using using immunohistochemistry in place of in situ hybridization.

The inventors also assessed whether known antiangiogenic compounds were recovered in the Xenopus screen. The LOPAC$^{1280}$ library harbors eight compounds (difluoromethylornithine, indirubin-3'-monoxime, 2-methoxyestradiol, minocycline hydrochloride, SU 4312, SU 5416, thalidomide, tyrphostin AG1478) with known antiangiogenic activitivities (Serbedzija et al., 1999; Tran et al., 2007). Three antiangiogenic compounds [difluoromethylornithine minocycline hydrochloride, thalidomide] are not considered, since they are highly hydrophilic and therefore poorly penetrate embryos (Tran et al., 2007). A screen of the LOPAC$^{1280}$ library using transgenic zebrafish expressing a fluorescent vascular reporter gene resulted in the recovery of three out of the five antiangiogenic compounds (indirubin-3'-monoxime, SU 4312, Tyrphostin AG1478) (Tran et al., 2007). In *Xenopus*, all five compounds [indirubin-3'-monoxime, 2-methoxyestradiol, SU 4312, SU 5416, Tyrphostin AG1478] scored as active in the phenotypic *Xenopus* screens (Tables 3 and 4). Importantly, the two VEGFR inhibitors SU4312 and SU5416 were identified as positive hits validating the screening procedure (FIG. 5m, n). Taken together, the analysis demonstrates that the phenotypic chemical library screening method is capable of efficiently identifying antiangiogenic compounds in *Xenopus* embryos. This occurs with higher efficiency and sensitivity than with the transgenic zebrafish reporter line. The phenotypic screening method is widely applicable to other aquatic lower vertebrate animal models as it does not require the generation of transgenic reporter lines. With regard to amphibians, the method is applicable to the subclass Lissamphibia, which includes all living amphibians. Lissamphibia consist of three orders: *Anura* (frogs and toads), *Urodela* or *Caudata* (newts, salamanders, and mudpuppies), and *Gymnophiona* or *Apoda* (caecilians). In a particular embodiment, the amphibian belongs to the genus *Xenopus*, which includes *Xenopus laevis* or *Xenopus tropicalis*.

Figure 6:
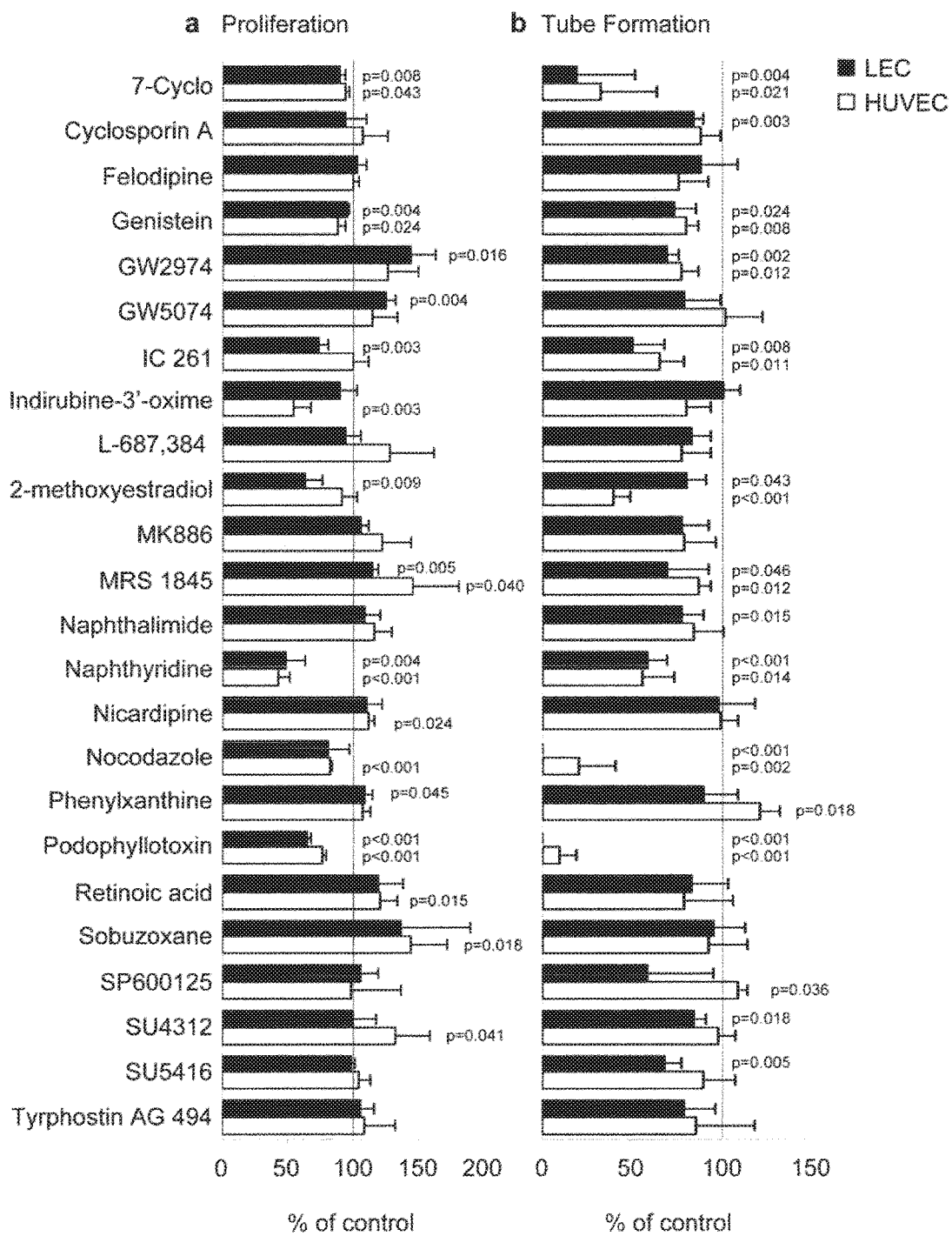
FIG. 6. Selective and cell-type specific in vitro responses of endothelial cells to treatment with small-molecule compounds. 24 compounds were tested in vitro on human lymphatic (LEC; black bars) and blood vascular (HUVEC; open bars) endothelial cell cultures for effects on cell proliferation and tube formation. (a) Results of the compound screens using cell proliferation assays. Compounds were screened at a dose of 10 µM in 0.1% DMSO. Control cultures were treated with 0.1% DMSO. (b) Results of the compound screens using tube formation assxys. Compounds were screened at a dose of 1 µM in 0.1% DMSO. Control cultures were treated with 0.1% DMSO. Abbreviations: 7-Cyclo: 7-cyclopentyl-5-(4-phenoxy)phenyl-7H-pyrrolo[2.3-d]pyrimidin-4-ylamine; L-687,384: L-687,384 hydrochloride; Naphthalimide: 4-amino-1,8-naphthalimide; Naphthyridine: 7-chloro-4-hydroxy-2-phenyl-1,8-naphthyridine; Nicardipine: Nicardipine hydrochloride; Phenylxanthine: 1,3-diethyl-8-phenylxanthine. Bars indicate mean values and standard deviations of three independently performed assays.

In the addition to the known antiangiogenic compounds, the inventors have identified 27 new compounds affecting vascular and/or lymphatic development in *Xenopus* embryos. A number of these compounds, such as nocodazole, podophyllotoxin, forskolin, and retinoic acid, are known to have broad effects on many cell types. Without intending to be bound by theory, the antiangiogenic activities observed for these compounds are likely the result of pleiotropic effects. The predicted biological functions of other recovered compounds implicate the requirement of various mechanisms, including hormone and cyclic nucleotide signaling, phosphorylation as well as $K^+$- and $Ca^{2+}$- channels for the normal development of blood vessels and/or lymphatics. Regarding the hits exhibiting only blood vascular system defects in vivo, this included compounds causing defective vasculogenesis, impaired angiogenesis, or VVN hypoplasia. Interestingly, the $Ca^{2+}$ ATPase inhibitor calmidazolium chloride and Raf1 kinase inhibitor GW5074, two compounds not previously known to exhibit activities on the vascular system, were found to act in a pro-angiogenic fashion by promoting ectopic, premature angiogenesis in *Xenopus* embryos (FIG. 3g, h, i, j). In addition, effects on the VVN were noticed (FIG. 3h, j). GW5074 was also tested in endothelial cell culture assays, where it promoted endothelial cell proliferation (FIG. 6). On the basis of in vitro and in vivo evidence, but without intending to be bound by theory, these compounds imply $Ca^{2+}$-ATPase and Raf kinase in the regulation of endothelial cell function. Furthermore, and without intending to be bound by theory, these small-molecule compounds may have the ability to substitute for mitogenic growth factors used to stimulate endothelial cell proliferation.

Figure 5:
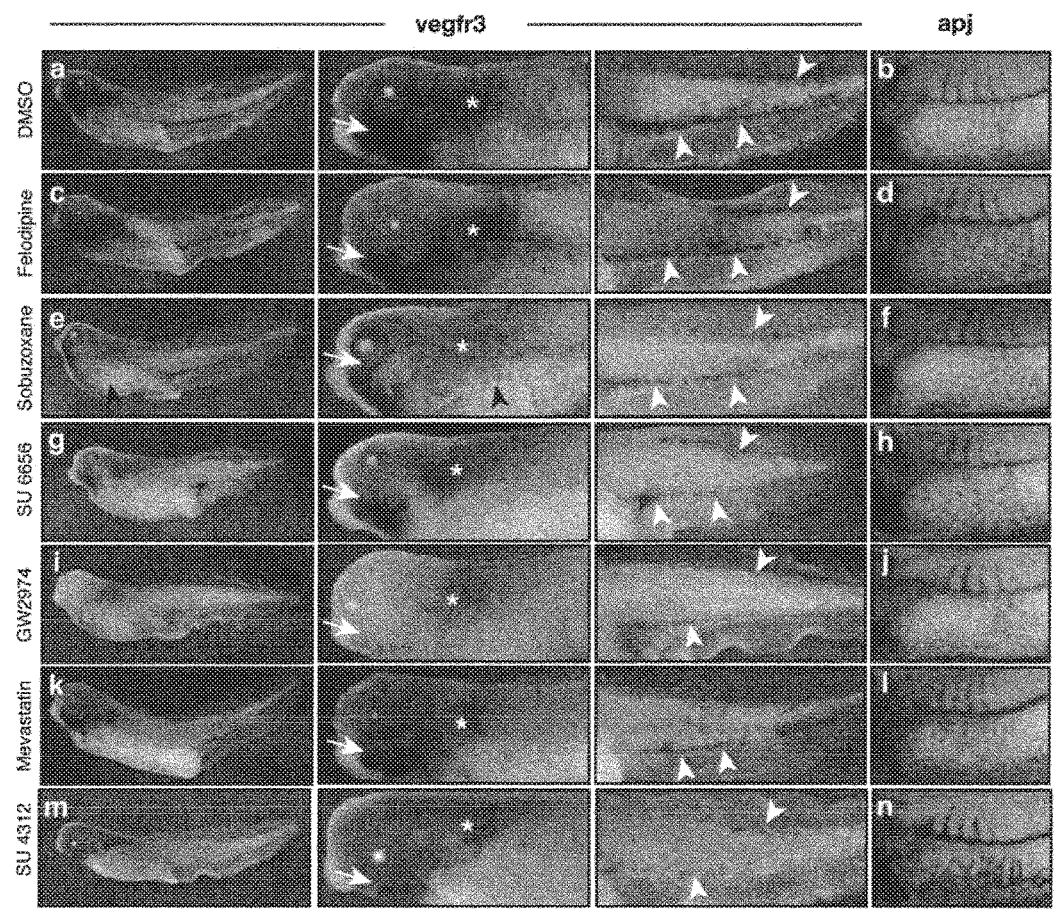
FIG. 5. Compounds specifically affecting lymph vessel development in *Xenopus* tadpoles. Control DMSO- (a, b) and compound-treated (c-n) *Xenopus* embryos were analyzed by whole mount in situ hybridization as described in the legend to FIG. 4. Close-up views of apj-stained embryos illustrate normal ISV angiogenesis and VVN development in the embryonic trunk. ALS, ALH, and PLVs are highlighted by arrows, asterisks, and arrowheads, respectively. (a, b) Normal ALS and ALH lymphatics, and PLVs. (c, d) Dysplastic ALH lymphatics. (e, f) Dysplastic ALS and ALH lymphatics, and hypoplastic PLVs. Note persistent vegfr3 expression in the VVN (black arrowhead). (g, h) Stunted ALS lymphatics, dysplastic, ALH lymphatics, and hypoplastic PLVs. (i, j) Impaired ALS lymphangiogenesis, stunted ALH lymphatics, and hypoplastic (k-n) Impaired ALS and ALH lymphangiogenesis, and hypoplastic PLVs.

Several compounds inhibiting preferentially lymphatic vascular development were identified in the assays, including several tyrosine kinase inhibitors (SU 4312, SU 6656, GW2974), and L-type calcium channel blockers (felodipine, nicardipine) (Table 9, FIG. 5). Treatment with the VEGF- and PDGF-receptor antagonist SU 4312 had the most potent effect on lymphatic vessel formation in vivo as demonstrated by the absence of VEGFR3-positive structures of the lymphatic system in *Xenopus* embryos (FIG. 5m). The blood vasculature remained largely unaffected (FIG. 5n). These results indicate that, at the concentration of 20 µM used in the *Xenopus* assay. SU 4312 targets in vivo primarily the VEGFC/VEGFR3 signaling pathway, which regulates embryonic lymphangiogenesis in tadpoles and mouse embryos (Karkkainen et al., 2004; Ny et al., 2005). At higher concentrations (>30 µM). SU 4312 will also exhibit moderate antiangiogenic effects as was recently demonstrated in zebrafish (Tran et al., 2007). Collectively, but without intending to be bound by theory, these findings indicate that SU 4312 may act in vivo primarily on lymphatic vessels. This also applies to the dual ErbB2 and EGF receptor tyrosine kinase inhibitor GW2974 and Src family kinase inhibitor SU 6656, which both exhibited antilymphatic activities in vitro and/or in vivo.

The role of calcium channels in lymphatic vessel formation and function has not been studied to date. The calcium channel blockers felodidipine and nicardipine have vasodilatory effects and are therefore widely used to treat hypertension. However, one bothersome side-effect of these older dihydropyridines is edema formation especially in the feet, legs, and ankles (Ram, 2006), which could indicate dysfunction of the lymphatic vasculature.

Figure 7:
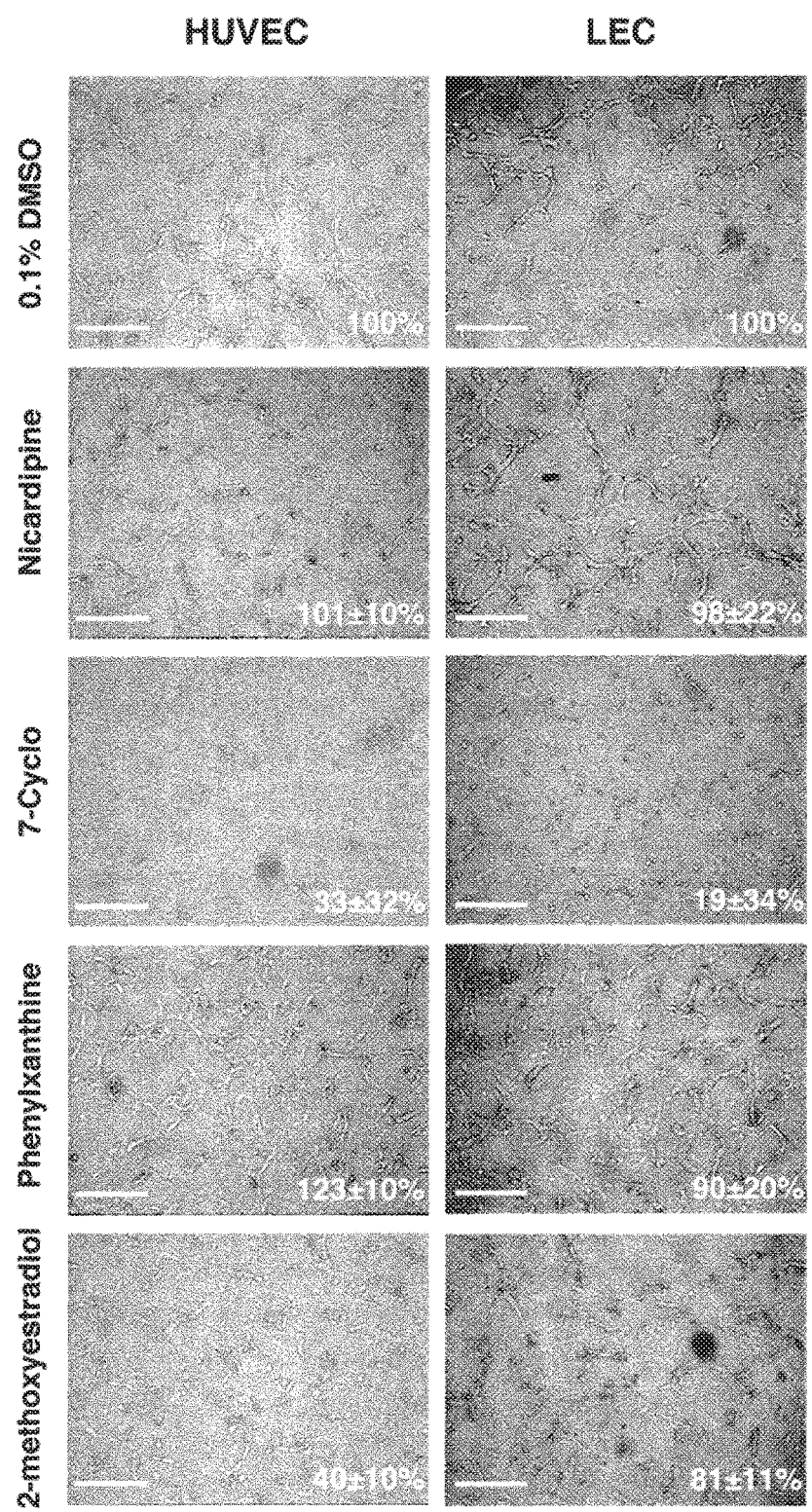
FIG. 7. Differential, cell-type specific effects of selected small-molecule compounds on endothelial tube formation. Confluent monolayers of HUVEC or LEC were overlaid with collagen type I gels containing the indicated compounds at a dose of 1 µM in 0.1% DMSO. Scale bars: 100 µm.

The majority of compounds with inhibitory effects on the vascular or lymphatic development in *Xenopus* also inhibited proliferation and/or tube formation of cultured human LEC and HUVEC (FIG. 6). 7-cyclo and naphthyridine, two compounds disrupting both blood and lymph vessel formation in vivo, also exhibited inhibitory activities for both HUVEC and LEC in vitro (FIG. 4c-f; FIG. 7). Furthermore, the inhibition of HUVEC tube formation in vitro correlates well with the in vivo observation of defective intersomitic vein angiogenesis. Despite these compelling examples, many compounds with in vivo bioactivity showed no effects in cell culture models indicating that the in vitro assays may fail to adequately reproduce all steps of vascular development (Table 10). The results indicate that in vitro cell-based chemical library screens are less reliable and lack sufficient predictive power to identify compounds with anti-angiogenic and/or -lymphatic activity in vivo. In contrast, *Xenopus* tadpoles allow high-throughput screening in a physiological context compared to traditional cell-based screens.

Figure 8:
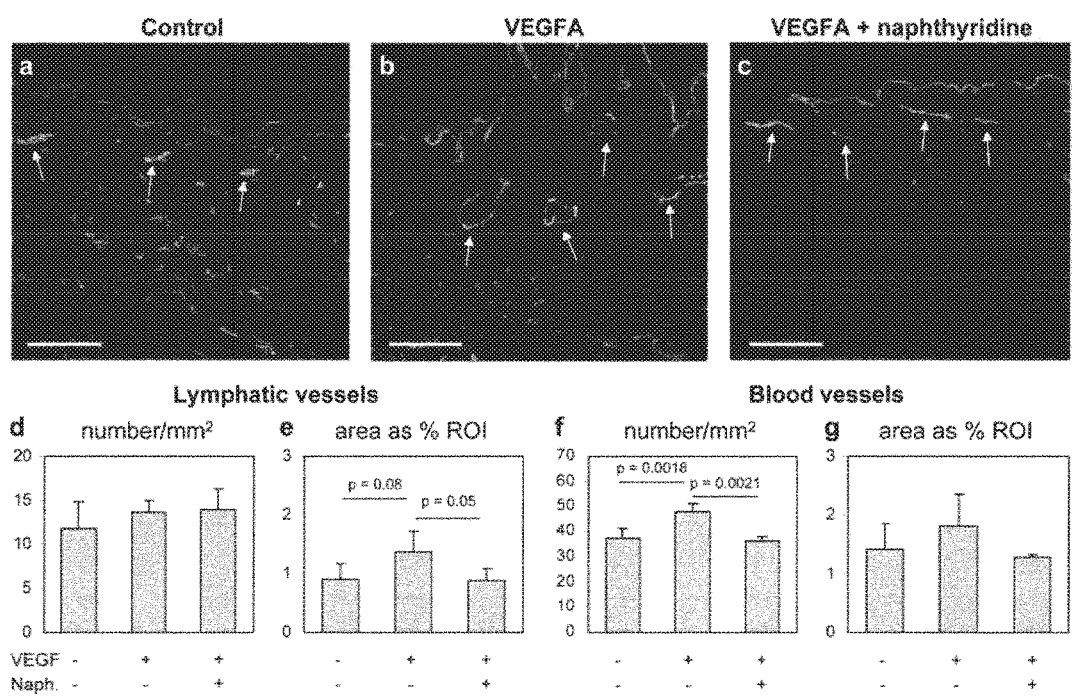
FIG. 8. The adenosine A1 receptor antagonist naphthyridine inhibits VEGFA-induced angiogenesis and lymphatic vessel enlargement in mice. VEGFA-containing Matrigel plugs were implanted subcutaneously into adult mice and the mice were subsequently treated systemically with naphthyridine or with vehicle control for 6 days. (a-c) Differential immunofluorescence analysis for the lymphatic-specific marker LYVE1 (green, examples highlighted by arrows) and the pan-vascular marker CD31 (red) demonstrated lymphatic vessel enlargement and enhanced numbers of blood vessels in the skin surrounding VEGFA-containing Matrigels (b), as compared with Matrigels containing PBS (a). Treatment with naphthyridine resulted in a reduction of blood vessel numbers and lymphatic vessel enlargement (c), (d-g) Quantitative image analyses confirmed that the density of lymphatic vessels was unchanged by VEGFA alone or by combined VEGFA and naphthyridine treatment (d). In contrast, the tissue area covered by lymphatic vessels surrounding VEGFA containing Matrigels was significantly reduced by treatment with naphthyridine (e). Treatment with naphthyridine also reduced the number of VEGFA-induced blood vessels (f) and the tissue area covered by blood vessels (g). Scale bars: 100 µm.

The inventors have also investigated the potential involvement of candidate compounds recovered from the *Xenopus* tadpole screens in (lymph)angiogenesis in mammals. Naphthyridine, an adenosine A1 receptor antagonists, inhibited blood and lymphatic vessel formation in tadpoles, which could also be recapitulated using in vitro endothelial cell proliferation and tube formation assays (FIG. 4e, f, FIG. 6). In a proof-of-principle study, naphtyridine was tested in an established mouse model of VEGFA-induced dermal neovascularization (FIG. 8). Remarkably, systemic treatment of mice with naphthyridine potently inhibited lymphatic vessel enlargement and angiogenesis indicating that adenosine A1 receptors do not only act antagonistically on amphibian vascular development but also disrupt adult mammalian (lymph)angiogenesis. The conservation of the in vivo activities between amphibians and mammals validates *Xenopus* embryos and tadpoles as relevant screening tools in drug discovery for human diseases.

Vascular growth and function are regulated by a complex interplay between different cell types and mediators, which cannot be sufficiently reproduced by in vitro culture systems. The use of *Xenopus* embryos has several advantages over mouse models of vascular development: Tadpoles only need little space and low-cost growth medium, and five tadpoles can be incubated simultaneously per well of a 48-well plate. Since in the early stages of development, nutrients, oxygen, and also small organic molecules freely diffuse through the skin, injections are not necessary. Moreover, tadpoles are not highly motile; thus, no anesthesia is needed for visual inspection. Importantly, treatment with small molecules revealed highly reproducible results, as the same phenotype was usually observed in all embryos treated with the same compound. Visual inspection is rapid and a single investigator can easily analyze 320 compounds per week. Zebrafish represents an alternative lower vertebrate animal model for whole organism-based drug discovery screens as it shares many advantages with *Xenopus* (Zon and Peterson, 2005). Most notably, zebrafish mutants with vascular defects have been used in large-scale chemical suppressor screens to identify small molecules conferring therapeutic benefits (Zon and Peterson, 2005). However, from an evolutionary perspective, amphibians are the animal models of choice as they have co-evolved with mammals for almost 100 million years longer than fish (Brändli, 2004). This fact may also provide an explanation for the low hit rate observed in a recently reported zebrafish-based screen of the LOPAC library for compounds with anti-angiogenic activities (Tran et al., 2007) and may account for the failure to identify known and novel antiangiogenic molecules, such as naphtyridine.

The instant examples demonstrate that the *Xenopus* embryo model in combination with a two-step screening method represents an effective, low-cost platform to identify novel pathways involved in angiogenesis and lymphangiogenesis, and to accelerate the discovery of novel drug-like small organic molecules. Despite the obvious differences in constitution and physiology between amphibians and humans, the *Xenopus* tadpole model represents a much-needed tool to bridge the gap in drug discovery between traditional in vitro and preclinical animal models.

Materials and Methods a) *Xenopus* Embryo Husbandry

In vitro fertilization and culture of wild-type and albino *Xenopus* embryos were performed as previously described (Brändli and Kirschner, 1995; Helbling et al., 1998). Embryos were raised in 0.1×MMR (1×MMR: 0.1 M NaCl, 2 mM KCl, 1 mM $MgSO_4$, 2 mM $CaCl_2$, 5 mM Hepes, pH 7.8) at room temperature and staged according to Nieuwkoop & Faber (Nieuwkoop and Faber, 1994). Any unfertilized, dead or malformed embryos were removed from the embryo cultures.

b) Chemical Library Screening and Confirmatory Testing

The LOPAC[1280] chemical library (Sigma, #LO2800, Lot No. 035K4701) containing 1,280 compounds (10 mM in DMSO) was used for the phenotype screening of *Xenopus* embryos. 10-μl aliquots of the chemicals were transferred from the mother plates with a liquid handling robot (Aquarius, Tecan) into 96-well tissue culture plates to generate diluted stock plates (2 mM in DMSO; 50 μl final volume). Wild-type, healthy *Xenopus* embryos were arrayed at stage 29-30 (35 hours post fertilization, hpf) into polystyrene flat-bottom 48-well tissue culture plates (BD Falcon #355078) (5 embryos per well) containing 1 ml 0.1×MMR. Once embryos reached stage 31 (37 hpf), 10-μl aliquots of the diluted chemicals were added to the wells. The final concentration of each chemical was 20 μM in the presence of 1% DMSO. The γ-secretase inhibitor compound E (Merck #565790; 20 μM) was used as a positive, edema-inducing control compound (R.E.K. & A.W.B, unpublished observation). Negative control wells contained embryos in screening medium and 0.1×MMR only. Embryos were treated with the chemicals in a humidified incubator at 23° C. over a timeframe of 4 days. Embryos were manually scored for the presence of edema or other morphological phenotypes using a teaching dissecting microscope (SV6; Carl Zeiss). Two investigators performed separately the scoring daily at stages 39 (56 hpf), 41 (76 hpf), 45 (98 hpf), and 47 (120 hpf). Dead embryos were removed and 100 μl of water was added daily to each well to compensate for fluid evaporation. Chemicals were considered to be active when at least 4 out of 5 embryos displayed the same phenotype (edema, lethality, or other phenotypes). All putative hits were retested and in each case comparable results were obtained. For imaging at the end of the experiments. *Xenopus* tadpoles were anesthetized with 0.05% tricaine (Sigma #A5040) in 0.1×MMR. Images were captured using a stereomicroscope (SteREO Lumar V12; Carl Zeiss) equipped with a digital camera (AxioCam Color; Carl Zeiss).

c) Secondary Chemical Screening

In follow-up studies, 65 chemicals from the LOPAC[1280] library that either induced edema formation or lethality were tested for their ability to interfere with blood vessel development and/or lymphangiogenesis in *Xenopus* embryos. All chemicals were purchased from Sigma and 10-mM stock solutions in DMSO were prepared. Chemicals were used at a final concentration of 20 μM in screening medium to treat homozygous albino *Xenopus* embryos, which lack natural pigmentation. Chemical treatments of embryos (n=7 per well) was initiated at stage 31 (37 hpf) and terminated at stages 35/36 (50 hpf) or 42 (80 hpf). Embryos were fixed in 4% paraformaldehyde and processed for whole mount in situ hybridization.

d) Whole Mount in situ Hybridizations

Whole mount in situ hybridizations and synthesis of dixoxigenin-labeled in situ hybridization probes were performed as described previously (Helbling et al., 1999; Saulnier et al., 2002). Where albino embryos were used, the bleaching step was omitted. Semi-automated whole mount in situ hybridizations were performed using the Biolane HTI machine (Hölle & Hüttner AG, Germany). Digoxigenin-labeled cRNA probes were generated from linearized plasmids encoding the blood vessel marker apj (Kälin et al., 2007) and lymph vessel marker vegfr3 (GenBank Acc. No. BM2611245). Sense strand controls were prepared from the plasmids and then tested negative by in situ hybridization. Images were captured using a stereomicroscope (SteREO Lumar V12; Carl Zeiss) equipped with a digital camera (AxioCam Color; Carl Zeiss). Composite figures were organized and labeled using Adobe Photoshop CS2 and Adobe Illustrator CS software.

e) Mammalian Cell Culture

Human umbilical vein endothelial cells (HUVEC) were purchased from PromoCell. Dermal lymphatic endothelial cells (LEC) were isolated from neonatal human foreskins and characterized as described previously (Hirakawa et al., 2003; Kajiya et al., 2005). HUVEC and LEC were cultured in endothelial basal medium EBM (Cambrex) supplemented with 20% fetal bovine serum (Invitrogen), antibiotic-antimycotics (100 U/ml penicillin, 100 μg/ml streptomycin, 250 ng/ml amphotericin; Invitrogen). 2 mM L-glutamine (Invitrogen), 10 μg/ml hydrocortisone (Fluka) and 25 μg/ml $N^6$,2'-O-dibutyryladenosine 3',5'-cyclic monophosphate sodium salt (Fluka) for up to eleven passages. LEC cultures were validated for lineage-specific cell differentiation by quantitative real-time RT-PCR (lymphatic vascular marker genes: PROX1, LYVE1, and PODOPLANIN1; blood vascular endothelial marker genes: VEGFR1 and VEGFC) and by immunocytochemistry (marker tested: CD31, LYVE1, and PROX1) as described previously (Hirakawa et al., 2003).

f) Chemical Treatments of Cell Cultures

Proliferation and tube formation assays were largely performed as described (Kajiya et al., 2005). To test for effects on cell proliferation, HUVEC and LEC ($3 \times 10^3$ cells) were seeded into fibronectin (10 ug/ml)-coated flat-bottom black 96-well tissue culture plates (#3603, Corning) and treated with selected chemicals at a screening dose of 10 µM in 0.1% DMSO or with 0.1% DMSO only. After 48 hours at 37° C., cells were incubated with 4-methylumbelliferylheptanoate (Sigma #M2514) as described (Kajiya et al., 2005). The intensity of fluorescence, which is proportional to the number of viable cells, was measured using a microplate reader (SpectraMax Gemini EM; Molecular Devices). The chemical treatments were performed in five replicates.

The effect of the selected chemicals on the formation of tube-like structures was performed as follows. Confluent monolayers of HUVEC and LEC were overlaid with 0.5 ml of neutralized isotonic bovine dermal collagen type I (1 mg/ml for LEC, 1.2 mg/ml for HUVEC; PureCol #5409, Inamed BioMaterials) containing either the selected chemical (1 µM in 0.1% DMSO) or vehicle only (0.1% DMSO). For 7-chloro-4-hydroxy-2-phenyl-1,8-naphthyridine (naphthyridine), the IC50 value on LEC tube formation was determined using the following compound doses: 0.2 µM, 0.4 µM, 0.55 µM, 0.7 µM, 1 µM, and 2 µM. After overnight incubation at 37° C. the treated cell cultures were fixed with 4% paraformaldehyde. Each chemical treatment was performed in triplicate and the experiment was repeated at least three times. Three representative images of hotspots with tube-like structures were taken per well using a digital camera (AxioCam MRm, Carl Zeiss) mounted on an inverted microscope (Axiovert 200M, Carl Zeiss). The length of the tube-like structures was measured using the IPLab software (BD Biosciences). For each experimental condition, results are represented as average total tube length (µm) per area (three image fields).

g) Matrigel Plug Implantation Assay

The mouse studies were conducted under protocols approved by the Veterinary Office of the Canton of Zurich, Switzerland (permit #123/2005). Nine week-old female wild-type FVB mice (Charles River) were used for the experiments (n=6 per group). Prior to Matrigel implantation, the mice were anesthetized by intraperitoneal injection of 200 µl of Dormitor (20 µg/ml medetomidine; Pfizer) and Narketan 10 (8 mg/ml ketamine; Vétoquinol). The left hip of the animals were shaved and subsequently Matrigel was implanted by intradermal injection of 100 µl of unpolymerized growth factor-reduced Matrigel (BD Biosciences) containing 0.5 mg/ml recombinant human VEGFA (#0081109; National Cancer Institute, USA). The mice were treated orally with either 200 µl PEG-400 (Fluka; pH adjusted to 5.2; control group) or with 200 µl PEG-400 containing 71.5 pg naphthyridine (3 mg/kg/day). Another control group of mice received Matrigel without VEGFA and was treated with 200 µl PEG-400. The treatment was given once daily for six days. Weight and appearance of animals was monitored daily. On the $7^{th}$ day, the Matrigel implants were removed from the euthanized mice for immunocytochemical examination. The Matrigel implants were frozen in Tissue-Tek O.C.T. compound (Sakura Finetek), sectioned, and processed as described previously (Kajiya et al., 2005). In brief, 6-µm frozen sections were fixed in −20° C. acetone for two minutes and in cold 80% methanol for five minutes, followed by incubation with antibodies against the lymphatic-specific marker LYVE1 (1:1,000; Millipore) and against the pan-endothelial marker CD3.1 (anti-mouse; 1:50; BD Biosciences). Corresponding secondary antibodies were labeled with Alexa 488 or Alexa 594 (Invitrogen). Nuclei were counterstained with 20 µg/ml Hoechst 33342 (Invitrogen). Sections were examined under an Axioskop 2 mot plus microscope and digital images were taken using an AxioCam MRc camera (Carl Zeiss). Three pictures each were taken of vascularized areas around the Matrigel implants (maximal distance from the implant: 500 µm). The vessel density, average vessel size and the average tissue area occupied by vessels were determined in CD31/LYVE1 stained sections using the IPLab software (BD Biosciences) as described (Kajiya et al., 2005).

h) Statistical Analyses

Results from in vitro cell assays are represented as mean±standard deviation (SD) of independently performed assays. Statistical analysis was performed by comparing means of biological replicates using the unpaired two-tailed student's t-test (Excel, Microsoft). Results obtained from the in vivo mouse experiments are shown as means±standard error of mean (SEM). The statistical significance was determined using the unpaired two-tailed student's t-test (GraphPad Prism Version 4 GraphPad Software). A value of P<0.05 was considered as significant.

Example 1

A Chemical Library Screen Identifies a Subset of Compounds with Pharmacological Activity in Xenopus Embryos A two-step whole organism-based chemical screening method was developed to rapidly identify novel small-molecule modulators of angiogenesis and lymphangiogenesis during Xenopus embryogenesis (FIG. 1). The Library of Pharmacologically Active Compounds (LOPAC$^{1280}$, Sigma-Aldrich) comprising 1,280 bioactive compounds was selected for the embryo-based screenings. The annotated compound library consists of marketed drugs, failed development candidates, and gold standards that have well-characterized activities. The compounds represent 56 pharmacological classes with diverse and experimentally validated biological mechanisms, such as G-protein coupled receptors (GPCR) and kinases (Rickardson et al., 2006).

The primary screening method used edema formation in compound-treated tadpoles as a rapid phenotypic read-out. Edemas present as abnormal fluid-filled swellings in any organ of the body. They are caused by imbalanced fluid homeostasis either by increased secretion of fluid into the interstitium or impaired removal of this fluid. The underlying pathophysiological causes include increased hydrostatic pressure or reduced oncotic pressure in the circulatory system, obstruction of the lymphatic system, and retention of sodium and water. Edema formation can therefore be used as a convenient indicator of either impaired cardiovascular, lymphatic, and/or excretory system functions.

Xenopus late tailbud embryos at stage 31 (37 hpf) were selected for compound treatment. This embryonic stage coincides with the onset of lymphatic system formation and intersomitic vein angiogenesis during Xenopus embryogenesis (Heibling et al., 2000; Ny et al., 2005). Embryos were arrayed into 48-well dishes (five per well) and treated with test compounds at a concentration of 20 µM in the presence of 1% DMSO. As a positive control, embryos were treated with compound E, a cell-permeable inhibitor of γ-secretase (Seiffert et al., 2000), which potently induces edemas (data not shown). All 48-well dishes also contained replicates of negative controls (1% DMSO). Embryos were monitored daily over a period of four days for edema formation. In addition, drug-induced lethality and other externally visible phenotypes were scored. On average, 320 compounds were screened per week. The phenotypes observed were highly reproducible as all embryos treated with a specific compound showed the same phenotype. Furthermore, all of the compounds generating hits were retested and yielded comparable results.

The majority (1,166 compounds; 91%) of the 1,280 compounds tested did not cause any discernable phenotypes in embryos and tadpoles until stage 47 (120 hpf), when treatments were terminated (Table 1). The remaining 114 (9%) compounds scored as hits. Fifty compounds representing 4% of the LOPAC$^{1280}$ library caused either embryonic or lethality without evidence of edemas. The first group included 32 compounds that were severely cytotoxic resulting in early embryonic lethality within 14 hours of compound treatment (Table 2). The second group consisted of 18 compounds that were lethal in tailbud embryos and/or tadpoles from at stage 37/38 (54 hpf) onwards (Table 3). Finally, 64 (5%) compounds causing specific, externally discernable phenotypes in embryos were identified. Edemas were observed after treatment with 48 (4%) of the 1,280 compounds tested (Table 4). In addition, 10 compounds affected skin pigmentation (Table 5) and 6 compounds caused other phenotypic changes (Table 6).

Example 2

Compounds with Comparable in vivo Activities Target Distinct Pharmacological Pathways The 1,280 compounds in the LOPAC library represent 56 distinct pharmacological classes of which 34 (61%) were active in the *Xenopus* screen (Table 7). Among the 114 active compounds, those affecting phosphorylation (30; 2.6%) were most prominently represented, followed by 9 (8%) interfering with the dopamine pathway, and 8 (7%) modulating $Ca^+$ channels. For seven pharmacological classes, which include phosphorylation, dopamine, and hormone signaling, a given compound was able to contribute to one of three distinct phenotype classes, 13 compound classes were contributing to at least two phenotype classes, whereas 14 were associated with a single phenotype class only. The latter included, for example, several representatives of the adenosine and cyclic nucleotide classes, which specifically caused edema in tadpoles.

Characteristic sets of active compound classes were associated with each phenotype class. For the sake of simplicity, only compound classes with two or more hits will be mentioned here in detail. Compounds causing cytotoxicity included modulators of phosphorylation (11 hits), intracellular calcium (2), leukotriene (2), and lipid signaling (2) (Table 2, Table 7). These cytotoxic hits represent 12-25% of the total compounds of their respective pharmacological classes. Compounds inducing lethality were mainly derived from the phosphorylation (6 hits), $Ca^{2+}$ channel (2), and neurotransmission (2) classes with hit rates ranging from 4-11% (Table 3, Table 7). The 48 edema-inducing compounds represent the largest subgroup of the 114 active compounds identified in the screen. Of these, modulators of phosphorylation (13 hits), $Ca^{2+}$ channels (6), cyclic nucleotides synthesis (3), transcription (3), as well as adenosine (3) and dopamine (3) signaling were the most prominent (Table 4, Table 7). This suggests that dysregulation of numerous signaling pathways contributes to edema formation. Finally, 50% of the compounds causing pigmentation defects in tadpoles were modulators of dopamine receptor signaling (5 hits; Table 5, Table 7). This finding is remarkable as it is consistent with the well-known role of dopaminergic neurons in the regulation of pigmentation in *Xenopus* tadpoles (Dulcis and Spitzer, 2008). Furthermore, it indicates that the experimental parameters chosen for the embryo-based chemical screen were optimal and sufficiently sensitive to recover agents targeting in vivo pharmacological pathways of known biological significance.

Example 3

Shared Anatomical Patterns of Edema Formation Arise from Pharmacological Interference of Distinct Sets of Molecular Pathways Edema formation in response to compound treatment may initially occur highly regionalized, i.e. restricted to a specific organ or tissue, before becoming generalized to the whole body. Hence, the anatomical distribution and the temporal onset of edemas induced by the 48 edema-inducing compounds were analyzed in greater detail. In particular, the question of whether compounds producing similar phenotypes interfere with one common molecular pathway or affect several ones was examined. Overall, it was observed that the initial development of edemas was restricted to distinct locations of the embryo. The most frequent locations were the pericardial and ventral areas, followed by the periocular and pronephric areas. For most compounds (39 out of 48), more than one tissue was affected by edema formation. This indicates that multiple target tissues exist for a given compound. On the basis of shared location of edema formation and severity of the observed phenotype, six phenotype classes were defined (Table 8). Importantly, each phenotype class was associated with a specific subset of edema-inducing compounds that in turn define unique sets of essential molecular pathways.

One third of the edema-inducing agents (16 compounds) gave rise to the phenotype class A (Table 8). These compounds induced both pericardial and ventral edemas (FIG. 2*a-f*). Frequently, a third site of edema formation, typically in periocular or pronephric locations, was also noticed (FIG. 2*b, d*). Periocular, pericardial, ventral, and pronephric edema often fused over time resulting in the formation of large, liquid-filled edemas occupying the entire abdomen of affected tadpoles (not shown). In addition, tadpoles treated with GW2974 or MRS 1845 manifested also with enlarged lymph hearts (FIG. 2*d, f*). Finally, the adenylate, cyclase activator forskolin caused the class A-characteristic pericardial, ventral, and proctodeal edemas, which were however accompanied by a dramatic shortening of the anterior-posterior body axis (FIG. 2*r*). In total, the class A edema-inducing compounds represented 10 distinct pharmacological mechanisms (Table 8). Most prominently, they included all six edema-inducing $Ca^{2+}$ channel blockers and two out of the three adenosine receptor A1 antagonists present in the chemical library.

Embryos of class B manifested with periocular and ventral edemas, and, frequently, also developed pronephric edemas (Table 8; FIG. 2*g, h*). Typically, compound treatment did not result in lethality. The 12 compounds inducing this particular edema phenotype targeted 7 distinct molecular pathways. Modulators of phosphorylation (5 hits) and antagonists of dopamine signaling (2 hits) were the most prominently represented pharmacological classes.

Pericardial edemas alone were the hallmark of phenotype class C (FIG. 2*i, j*). Edema formation occurred as early as stage 33/34 followed by lethality usually before stage 45.

The compounds affected eight distinct molecular pathways and include inhibitors of phosphorylation (2 hits) and compounds targeting the cytoskeleton (2 hits; Table 8). Phenotype class D was defined by highly characteristic periocular edemas that were accompanied by other sites of edema formation. Increased fluid accumulation in periocular edemas caused subsequently the protrusion or bulging out of the eyes, a condition reminiscent of enophthalmos (FIG. 2k, l). The active compounds targeted three distinct mechanisms: apoptosis, gene regulation, and phosphorylation.

Embryos falling into phenotype class E were characterized by the presence of both cerebral and pronephric edemas (Table 8; FIG. 2m, n). Interestingly, all three compounds target retinoic acid receptors (RAR) suggesting that this edema phenotype is caused by dysregulation of RAR signaling. Finally, phenotype class F represents edema-inducing compounds that manifested with a heterogeneous range of edema types (Table 8; FIG. 2o-q). For example, genistein induced edemas localized to the tail tip (FIG. 2q). Despite the heterogeneity of edemas, all compounds were found to interfere with a single pharmacological class, protein phosphorylation.

Taken together, the analysis indicates that a given edema phenotype may arise from dysregulation of one or more distinct molecular pathways as demonstrated by the use of defined pharmacological agents. In addition, the fact that compounds targeting the same common molecular pathway (i.e. $C^{2+}$ channels and adenosine A1 receptors) frequently manifest with the same characteristic edema phenotype further underscores the validity and robustness of the whole-embryo based chemical library screening method.

Example 4

Figure 3:
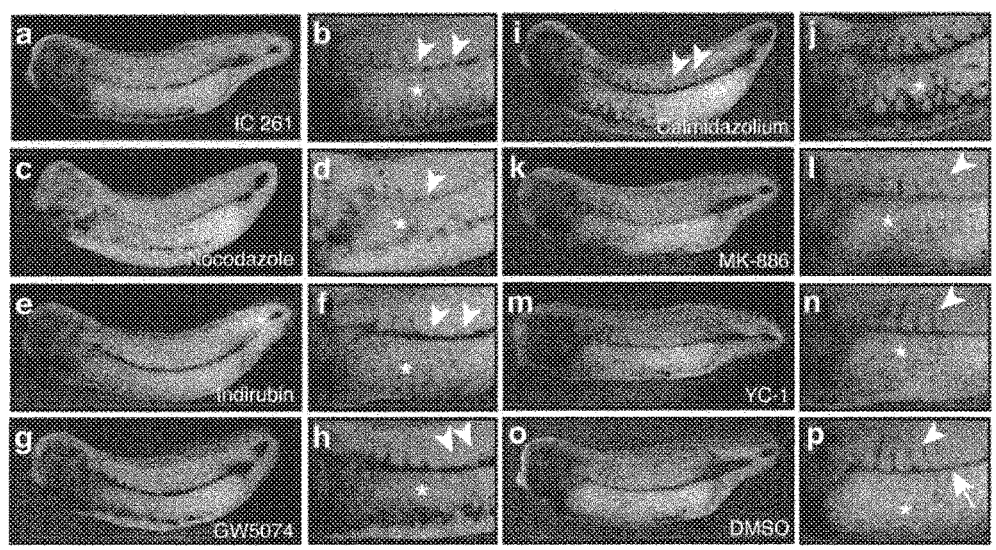
FIG. 3. Compounds affecting distinct aspects of blood vessel development in vivo. Compound-treated (a-n) and control DMSO-treated *Xenopus* embryos (o, p) were analyzed by whole mount in situ hybridization for expression of the vascular marker gene apj. Stage 35/36 embryos are shown in lateral views with anterior to the left. Close-up views of the trunk illustrate the morphology of the blood vessels. Compound names are indicated. (a-d) Hypoplastic VVN (asterisks) and PCV (arrowheads). (e, f) Lack of ISVs (arrowheads). Note that assembly of PCV and VVN (asterisk) is unaffected. (g, h) Ectopic ISV (arrowheads) and dysplastic VVN (asterisk). (i, j) Ectopic ISV (arrowheads) and hyperplastic VVN (asterisk). (k-n) Hypoplastic, dispersed VVN (asterisks), but normal ISV angiogenesis (arrowheads). (o, p) Control embryos with normal VVN (asterisk), PCV (arrow), and ISV (arrowhead). Abbreviations: Calmidazolium, calmidazolium chloride; Indirubin, indirubin-3'-oxime.
Figure 4:
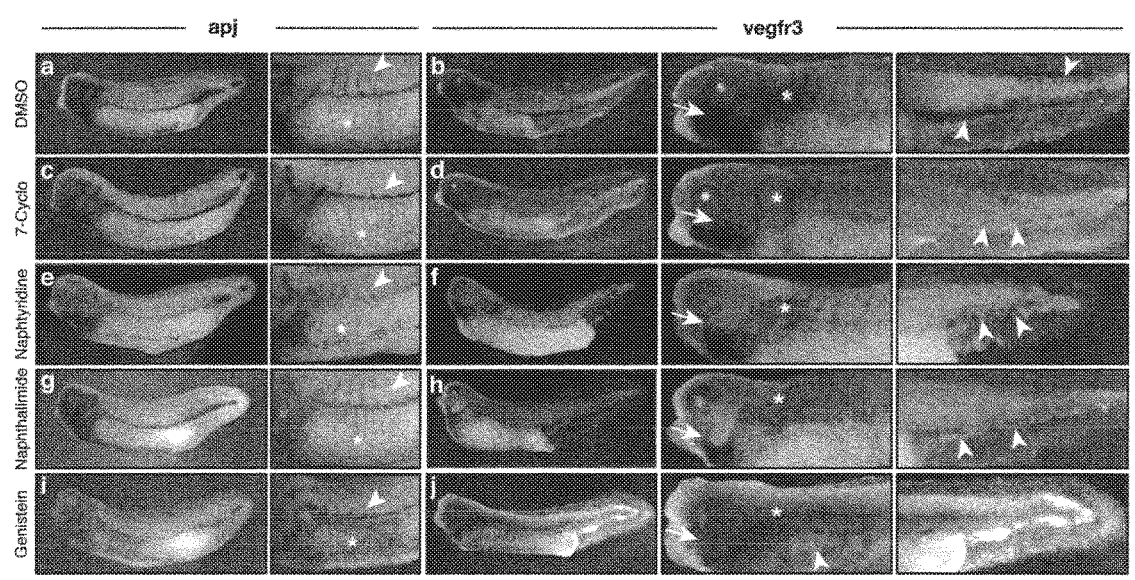
FIG. 4. Compounds affecting blood and lymph vessel development in *Xenopus* tadpoles. Control DMSO- (a, b) and compound-treated (c-j) *Xenopus* embryos were analyzed by whole mount in situ hybridization for expression of the blood vascular marker gene apj at stage 35/36 and the lymphatic marker gene vegfr3 at stage 42. Panels of the embryonic blood vasculature (apj) are accompanied by close-up views illustrating ISV angiogenesis and VVN development in the embryonic trunk. The panels visualizing the developing lymphatic system (vegfr3) include close-ups of the head and midtrunk region (middle panels) for the anterior lymph sacs (ALS) and the anterior lymph hearts (ALH), and enlargements (left panels) of the tail for posterior lymph vessels (PLV). (a) Normal ISVs (arrowhead) and VVN (asterisk). (b) Normal ALS (arrow), ALH (asterisk), and PLV (arrowheads). (c) Stunted ISVs (arrowhead), normal VVN (asterisk). (d) Hypoplastic PLV (arrowheads), impaired ALS (arrow) and ALH (asterisk) lymphatics. (e) Stunted ISV (arrowhead), hypoplastic VVN (asterisk). (f) Stunted ALS lymphatics (arrow), dysplastic ALH lymphatics (asterisks), hypoplastic PLV (arrowheads). (g) Normal ISV (arrowhead), hyperplastic VVN. (h) Hypoplastic PLV (arrowheads), impaired ALS (arrow) and ALH (asterisks) lymphatics. (i) Stunted ISV (arrowhead), hyperplastic VVN. (j) Complete lack of ALS (arrow), ALH (asterisk) and tail lymphatics. Note that vegfr3 expression persists in the VVN (arrowhead). Abbreviations: 7-Cyclo, 7-Cyclopentyl-5-(4-phenoxy)phenyl-7H-pyrrolo[2,3-d]pyrimidin-4-ylamine; Naphthalimide, 4-amino-1,8-naphthalimide; Naphthyridine, 7-chloro-4-hydroxy-2-phenyl-1,8-naphthyridine.

Small-Molecule Compounds Affecting Blood Vessel Development and Angiogenesis 48 compounds that induced edema in Xenopus tadpoles were identified (Table 2. Table 8) and 18 causing lethality at stage 37/38 (54 hpf) or later (Table 3). Together, the 66 compounds comprise 5.1% of all compounds present in the LOPAC library. Edema formation or late-stage lethality may result from excretory system defects, (cardio)vascular and/or lymphatic vascular pathologies. Semi-automated whole-mount in situ hybridization was next used to visualize the development of blood and lymphatic vessels in Xenopus embryos treated with hits from the primary screen. apj and vegfr3 (flt3) were used as marker genes for the blood (Kälin et al., 2007) and lymphatic vasculature (Ny et al., 2005), respectively Xenopus embryos were treated at stage 31 with 65 selected compounds at a concentration of 20 µM each. Embryos were fixed for in situ hybridization either at stage 35/36 to analyze vasculogenesis and intersomitic vein angiogenesis defects or at stage 42 to evaluate possible defects in lymph vessel development (FIGS. 3-5). It was found that 32 (49%) out of 65 compounds tested interfered with lymphatic and/or blood vascular development. 18 compounds blocked selectively blood vessel development, six compounds interfered with both blood and lymphatic vessel development, and eight compounds affected lymphatic development only (see Table 9 for summary).

With regard to the blood vascular defects, we identified four different classes: (1) Inhibition of vasculogenesis, as evidenced by hypoplasia of the vitelline vein network (VVN) and posterior cardinal veins (PCV) and absence of intersomitic veins (ISV); (2) Inhibition of angiogenesis, as reflected by defective ISV outgrowth and normal PCV; (3) Ectopic angiogenic sprouting of the ISV and VVN defects; and (4) hypoplasia of the VVN.

Compounds that interfered with blood vessel vasculogenesis and PCV assembly included the casein kinase 1 inhibitor IC 261 (FIG. 3a, b) and nocodazole, which disrupts cytoskeleton assembly (FIG. 3c, d). Both of these compounds also impaired development of the ISV and VVN (equivalent to the extraembryonic vasculature of the avian chorio-allantoic membrane and the mammalian yolk sac). Similar effects were observed after treatment with the tyrosine kinase inhibitor tyrphostin AG 494, 2-methoxyestradiol, the cytoskeleton inhibitor podophyllotoxin, the Cdc25 phosphatase inhibitor NSC 95397, and the dual cyclooxygenase and 5-lipoxygenase inhibitor meclofenamic acid (Table 9).

Angiogenesis inhibitors, as evaluated by the ability of compounds to block ISV outgrowth, included indirubin-3'-oxime, a cyclin dependent kinase inhibitor (FIG. 3e, f), and the VEGF receptor phosphotyrosine kinase inhibitor SU 5416 (Table 9), which is in agreement with previous studies in zebrafish (Bayliss et al., 2006; Parng et al., 2002; Tran et al., 2007). Retinoic acid, the adenylate cyclase activator forskolin, and the angiotensin receptor 1 agonist L-162.313 were further identified as potent inhibitors of developmental angiogenesis (Table 9).

Two compounds induced VVN defects and promoted premature angiogenic sprouting of intersomitic veins. After treatment with the Raf1 kinase inhibitor GW5074 (FIG. 3g, h), the VVN was dysplastic and—instead of forming a regular vessel network—the blood vascular endothelial cells were dispersed throughout the ventral parts of the embryo. Moreover, thin ectopic ISV sprouting was evident in the posterior parts of the PCV when compared to DMSO-treated control embryos (FIG. 3g, h, o, p). This ectopic sprouting phenotype was even more pronounced after treatment with the calmodulin-dependent $Ca^{2+}$ ATPase inhibitor calmidazolium chloride (FIG. 3i, j, o, p). In addition, the blood vessels, including the VVN, were larger and fused, representing hyperplastic vasculature. This hyperplastic endothelial phenotype is reminiscent of the phenotype observed after overexpression of vegfa in Xenopus embryos (Kälin et al., 2007).

A fourth group of compounds only interfered with the assembly of the VVN. The leukotriene synthesis inhibitor MK-886 led to hypoplasia of the VVN, but did not interfere with PCV assembly and ISV outgrowth (FIG. 3k, l). Similarly, treatments with the NO-independent guanylyl cyclase activator YC-1 (FIG. 3m, n), resulted in dispersed, punctuated patterns of VVN endothelia, which might indicate a block of endothelia cell proliferation or VVN assembly (Pyriochou et al., 2006). Other compounds of this group include the phosphodiesterase inhibitor zardaverine, and the cyclin-dependent protein kinase inhibitor purvalanol A (Table 9).

Example 5

Small-Molecule Inhibitors of Blood and Lymphatic Vessel Development

Both blood and lymphatic vessel malformations were noticed in Xenopus embryos and tadpoles after treatment with seven compounds (Table 9). In normal control embryos, three primary sites of lymphatic system development can be observed: the anterior lymph sacs (ALS) of the head, the region of the anterior lymph hearts (ALH) in the trunk, and the posterior lymph vessels (PLV) in the tail (FIG. 4b). Along with the analysis for blood vessel defects, these areas in compound-treated embryos were assessed specifically for abnormalities in early lymphatic vessel development. Based on this differential analysis, two general compound-induced phenotype classes were identified: compounds affecting both blood vessel and lymph vessel formation, and compounds disrupting selectively lymph vessel development only (Table 9).

The former phenotype class was comprised of six compounds. The src family tyrosine kinase inhibitor 7-cyclopentyl-5-(4-phenoxy)phenyl-7H-pyrrolo(2,3-d)pyrimidin-4-ylamin (in short: 7-Cyclo) interfered with angiogenic ISV sprouting but not with VVN assembly (FIG. 4c). Formation of ALS and ALH rudiments occurred, but lymphangiogenesis was strongly suppressed and the lymph vessel assembly in the tadpole tails was disrupted (FIG. 4d). The A1 adenosine receptor antagonist 7-chloro-4-hydroxy-2-phenyl-1,8-naphthyridine (in short: naphthyridine) interfered not only with ISV angiogenesis but also with VVN assembly (FIG. 4e). At later stages, tadpoles displayed stunted, disorganized lymphatic vessels arising from the ALS and ALH, and only a few LECs, but no lymph vessels, were detected in the tail (FIG. 4f). Similar vascular phenotypes were observed after treatment with the JNK inhibitor SP600125 (Table 9). A subgroup of three compounds manifested with lymphangiogenesis defects accompanied by VVN hyperplasia. Treatment with the adenosine A1 receptor antagonist 1,3-Diethyl-8-phenylxanthine or the poly(ADP-ribose) polymerase inhibitor 4-amino-1,8-naphthalimide caused hyperplasia of the VVN, while ISV angiogenesis occurred unaffected (FIG. 4g, not shown). Interestingly, lymphangiogenesis was largely suppressed (FIG. 4h, not shown). Treatment with the tyrosine kinase inhibitor genistein induced a severe blood vessel phenotype with stunted ISVs and hyperplastic VVN (FIG. 4i). At later stages, blood vessels were readily detected, whereas lymphatic vessels and LECs were absent (FIG. 4j). This suggests that genistein may interfere with the specification of lymphatic cell lineages.

Example 6

Small-Molecule Inhibitors of Lymphatic Vessel Development

Eight compounds that specifically inhibited lymphatic vessel development without affecting the blood vasculature were recovered from the chemical library screen (Table 9; FIG. 5). Each compound induced highly characteristic lymphatic defects ranging from subtle regional lymph vessel dysplasia (FIG. 5c) to severe, widespread disruption of lymph vessel development (FIG. 5i, k, m). The L-type calcium channel blocker felodipine caused abnormal, dysplastic lymphatic vessel sprouting without affecting other areas of lymphangiogenesis (FIG. 5c). Treatment with the DNA topoisomerase II inhibitor sobuzoxane and the $Ca^{2+}$ channel blocker nicardipine resulted in the formation of discontinuatous, dysplastic lymphatic vessels (FIG. 5e, not shown). In addition, vegfr3 expression persisted in the VVN of subuzoxane-treated embryos (FIG. 5e). The src family kinase inhibitor SU 6656 and the $K^+$ channel blocker dequalinium dichloride resulted in embryos with poorly developed, stunted lymphatics emerging from the ALS and ALH and hypoplastic PLV (FIG. 5g, not shown). The most severe defects in lymphatic vessel development were observed with three compounds—the inhibitor of protein prenylation mevastatin, and the tyrosine kinase inhibitors GW2974 and SU 4312 (FIG. 5i-m). After compound treatment, the three primary sites of lymphatic vessel development (ALS, ALH, and PLV) were detectable, but lymphangiogenesis was largely suppressed and the assembly of lymphatics in the tail was disrupted. This phenotype was most pronounced after treatment with SU 4312, which is known as a VEGF receptor-1/-2 (VEGFR) inhibitor (FIG. 5m). Interestingly, blood vascular development is critically dependent on VEGFR-1/-2 signaling, but appears to be unaffected in SU 4312-treated embryos as demonstrated by normal angiogenic ISV outgrowth (FIG. 5n). This indicates that, at the concentrations used here, SU 4312 selectively disrupts lymphangiogenesis by inhibiting VEGFC/VEGFR-3 signaling in vivo.

Example 7

Effects of Small-Molecular Compounds on in vitro Endothelial Cell Proliferation and Tube Formation The whole-organism based chemical library screens resulted in the identification of 32 compounds that interfered with lymphatic and/or blood vascular development in *Xenopus* tadpoles. It was next asked whether the in vivo activities of the compounds extended also to mammalian endothelia and whether the compounds interfered directly with endothelial cell functions. To address these points, 24 compounds were selected, and proliferation and tube formation assays, two important steps in vessel formation, were conducted using human lymphatic endothelial cell (LEC) and umbilical vein endothelial cell (HUVEC) cultures. Compounds were selected for in vitro testing on the basis that they represented different classes of in vivo active compounds (Table 10). The list included 19 compounds inducing edema in *Xenopus* tadpoles and 4 compounds (indirubin-3'-oxime, MK-886, SP600125, and SU 5416) causing lethality. Finally, the signal receptor ligand L-687,384 was chosen as it did not affect vascular development in *Xenopus* embryos.

The cell proliferation assays were performed by treating the endothelial cell cultures with compounds at a screening dose of 10 μM in 0.1% DMSO for 48 hours (FIG. 6a; Table 10). Nine compounds were scored as having marginal or no effects in the endothelial cell proliferation assays (85-115% of control) regardless of the cell type tested. Nine compounds moderately promoted cell proliferation (>115-150% of control). This includes three compounds (GW2974, retinoic acid, sobuzoxane) stimulating endothelial cell proliferation in both cell types tested. Five compounds (L-687,384, MK-886, MRS 1845, naphthalimide, SU 4312) promoted proliferation in HUVEC but not LEC cultures; and only one, GW5074, was selective for LEC cultures. Six compounds decreased endothelial cell proliferation in vitro. Podophyllotoxin and nocodazole inhibited moderately (65-82% of control), whereas naphthyridine strongly suppressed (42-48% of control) LEC and HUVEC proliferation. Interestingly, the remaining three compounds disrupted proliferation in a cell type-specific manner. IC 261 and 2-methoxyestradiol inhibited preferentially LEC proliferation, whereas indirubin-3'-oxime selectively blocked HUVEC proliferation consistent with a previous report (Tran et al., 2007).

The effects of the selected compounds on endothelial tube formation was assessed after over treatment of LEC and HUVEC cultures at a compound concentration of 1 μM in 0.1% DMSO. The length of the tube-like structures was measured using the IPLab software. 14 out of 24 compounds tested had comparable effects in both cell types tested. These include four compounds (cyclosporin A, nicardipine, sobuzoxane, SU 4312) with either no or only marginal effects on tube formation (85-115% of control tube length) (FIG. 6b). As an example, nicardipine is shown in FIG. 7. Moderate inhibition of tube formation (50-85% of control) in both cell types was observed with seven compounds (genistein, GW2974, IC 261, L-687,384, naphthyridine, MK-886, retinoic acid) (FIG. 6b). Finally, three compounds (7-cyclo, nocodazole, podophyllotoxin) were identified as strong inhibitors of endothelial tube formation (<35% of control) irrespective of the cell type tested (FIG. 6b, 7). The remaining ten compounds showed differential, cell-type specific effects on tube formation. Four compounds acted preferentially on HUVEC cultures. Phenylxanthine promoted HUVEC tube formation (123% of control for HUVEC versus 90% for LEC) (FIG. 7). In contrast, indirubin-3'-oxime, felodipine, and 2-methoxyestradiol blocked tube formation preferentially in HUVEC cultures. This was most apparent after 2-methoxyestradiol treatments when HUVEC tube formation was 40% of control, while LEC cultures were only moderately affected (80% of control) (FIG. 7). Interestingly, none of the compounds tested selectively promoted LEC tube formation, but six compounds (GW5074, MRS 1845, naphthalimide, oligomycin A, SP600125, SU 5416, tyrphostin AG 494) preferentially blocked tube formation in LEC rather than HUVEC cultures (FIG. 6b). The differences were most striking with SP600125 (59% of control for LEC versus 110% for HUVEC).

A comparison of the results from the in vitro and in vivo compound screens is shown in Table 10. Interestingly, only two compounds (cyclosporin A, nicardipine) at the concentrations tested here had little or no activity in the in vitro assays, indicating that many of the in vivo active compounds also interfered with endothelial cell functions in vitro. The predictive power of the in vitro assays was however limited. For example, three out of the five compounds affecting lymphangiogenesis in vivo had no activity in LEC-based in vitro assays. Notably, this included also the VEGF receptor antagonist SU 4312, which robustly blocks lymphangiogenesis in vivo (FIG. 5m).

Example 8

Naphthyridine Inhibits VEGFA-Induced (lymph)angiogenesis in Mice

The adenosine A1 receptor antagonist naphthyridine was identified as a novel inhibitor of lymphatic and blood vessel formation in Xenopus tadpoles and in vitro cellular assays, where it acted anti-mitogenic and impaired endothelial tube formation. It was determined that naphtyridine inhibited LEC tube formation with an $IC_{50}$ of 1.3 μM±0.1 μM (data not shown). To investigate whether naphthyridine might also inhibit mammalian angiogenesis and/or lymphangiogenesis in vivo, VEGFA-containing Matrigel plugs were implanted subcutaneously into adult mice and treated these mice systemically with naphthyridine (3 mg/kg/day) or with vehicle control for 6 days. In agreement with previous results (Hong et al., 2004), differential immunofluorescence analysis for the lymphatic-specific marker LYVE1 and the panvascular marker CD31 demonstrated lymphatic vessel enlargement in the skin surrounding VEGFA-containing Matrigels, as compared with control Matrigels only containing PBS (FIG. 8a, b). Treatment with naphthyridine resulted in a reduction of blood vessel numbers and lymphatic vessel enlargement (FIG. 8c). The quantitative image analyses shown in FIG. 8d-g confirmed that the tissue area covered by lymphatic vessels surrounding VEGFA containing Matrigels was significantly reduced by treatment with naphthyridine in comparison to the PBS control (1.36±0.36% versus 0.89±0.18%, p=0.05; FIG. 8e), while the density of lymphatic vessels was unchanged by VEGFA or naphthyridine treatment (FIG. 8d). Treatment with naphthyridine also reduced the number of VEGFA-induced blood vessels (36.49±1.49 versus 47.93±3.55; p=0.0021; FIG. 8f) and resulted in a reduction of the tissue area covered by blood vessels (FIG. 8g). It can be concluded that the ability of naphthyridine to inhibit lymph and blood vessel angiogenesis is conserved between Xenopus and mammals.

All of the above-cited references and publications are incorporated by reference herein in their entireties.

Those skilled in the art will recognize, or be able to ascertain using no more than routine experimentation, numerous equivalents to the specific method and reagents described herein. Such equivalents are considered to be within the scope of this invention and are covered by the following claims.

REFERENCES

Alitalo, K., Tammela, T., and Petrova, T. V. (2005). Lymphangiogenesis in development and human disease. Nature 438, 946-953.

Bayliss, P. E., Bellavance, K. L., Whitehead, G. G., Abrams, J. M., Aegerter, S., Robbins, H. S., Cowan, D. B., Keating, M. T., O'Reilly, T., Wood, J. M., et al. (2006). Chemical modulation of receptor signaling inhibits regenerative angiogenesis in adult zebrafish. Nat Chem Biol 2, 265-273.

Brändli, A. W. (2004). Prospects for the Xenopus embryo model in therapeutics technologies. Chimia 58, 695-702.

Brändli, A. W., and Kirschner, M. W. (1995). Molecular cloning of tyrosine kinases in the early Xenopus embryo: identification of Eck-related genes expressed in cranial neural crest cells of the second (hyoid) arch. Dev Dyn 203, 119-140.

Carmeliet, P. (2003). Angiogenesis in health and disease, Nat Med 9, 653-660.

Chang, S., Bray. S. M., Li, Z., Zarnescu, D. C., He, C., Jin, P., and Warren, S. T. (2008). Identification of small molecules rescuing fragile X syndrome phenotypes in Drosophila. Nat Chem Biol 4, 256-263.

Christensen, E. I., Raciti. D., Reggiani, L., Verroust, P. J., and Brandli, A. W. (2008). Gene expression analysis defines the proximal tubule as the compartment for endocytic receptor-mediated uptake in the Xenopus pronephric kidney. Pflugers Arch 456, 1163-1176.

Cleaver, O., and Krieg, P. A. (1998). VEGF mediates angioblast migration during development of the dorsal aorta in Xenopus. Development 125, 3905-3914.

Cueni, L. N., and Detmar, M. (2006). New insights into the molecular control of the lymphatic vascular system and its role in disease. J Invest Dermatol. 126, 2167-2177.

Dadras, S. S., Lange-Asschenfeldt, B., Velasco, P., Nguyen, L., Vora, A., Muzikansky, A., Jahnke, K., Hauschild, A., Hirakawa, S., Mann, M. C., et al. (2005). Tumor lymphangiogenesis predicts melanoma metastasis to sentinel lymph nodes. Mod Pathol. 18, 1232-1242.

Diamandis, P., Wildenhain, J., Clarke, I. D., Sacher, A. G., Graham, J., Bellows, D. S., Ling, E. K., Ward, R. J., Jamieson, L. G., Tyers, M., et al. (2007). Chemical genetics reveals a complex functional ground state of neural stem cells. Nat Chem Biol 3, 268-273.

Duleis, D., and Spitzer, N. C. (2008). Illumination controls differentiation of dopamine neurons regulating behaviour. Nature 456, 195-201.

Helbling, P. M., Saulnier, D. M., and Brändli, A. W. (2000). The receptor tyrosine kinase EphB4 and ephrin-B ligands restrict angiogenic growth of embryonic veins in *Xenopus laevis*. Development 127, 269-278.

Helbling, P. M., Saulnier, D. M., Robinson, V., Christiansen, J. H., Wilkinson, D. G., and Brändli, A. W. (1999). Comparative analysis of embryonic gene expression defines potential interaction sites for *Xenopus* EphB4 receptors with ephrin-B ligands. Dev Dyn 216, 361-373.

Helbling, P. M., Tram C. T., and Brändli, A. W. (1998). Requirement for EphA receptor signaling in the segregation of *Xenopus* third and fourth arch neural crest cells. Mech Dev 78, 63-79.

Hirakawa, S., Brown, L. F., Kodama, S., Paavonen, K., Alitalo, K., and Detmar, M. (2007). VEGF-C-induced lymphangiogenesis in sentinel lymph nodes promotes tumor metastasis to distant sites. Blood 109, 1010-1017.

Hirakawa, S., Hong, Y. K., Harvey, N., Schacht, V., Matsuda, K., Libermann, T., and Detmar, M. (2003). Identification of vascular lineage-specific genes by transcriptional profiling of isolated blood vascular and lymphatic endothelial cells. Am J Pathol 162, 575-586.

Hirakawa, S., Kodama, S., Kunstfeld, R., Kajiya, K., Brown, L. F., and Delmar, M. (2005). VEGF-A induces tumor and sentinel lymph node lymphangiogenesis and promotes lymphatic metastasis. J Exp Med. 201, 1089-1099.

Hong, Y. K., Lange-Asschenfeldt, B., Velasco, P., Hirakawa, S., Kunstfeld, R., Brown, L. F., Bohlen, P., Senger, D. R., and Detmar, M. (2004). VEGF-A promotes tissue repair-associated lymphatic vessel formation via VEGFR-2 and the alpha1beta1 and alpha2beta1 integrins. Faseb J 18, 1111-1113.

Howland, R. B. (1916). On the Effect of Removal of the Pronephros of the Amphibian Embryo. Proc Natl Acad Sci USA 2, 231-234.

Kajiya, K., Hirakawa, S., Ma, B., Drinnenberg, I., and Detmar, M. (2005). Hepatocyte growth factor promotes lymphatic vessel formation and function. Embo J 24, 2885-2895.

Kahn, R. E., Kretz, M. P., Meyer, A. M., Kispert, A., Heppner, F. L., and Brändli, A. W. (2017). Paracrine and autocrine mechanisms of apelin signaling govern embryonic and tumor angiogenesis. Dev Biol 305, 599-614.

Karkkainen, M. J., Haiko, P., Sainio, K., Partanen, J., Taipale, J., Petrova, T. V., Jeltsch, M., Jackson, D. G., Talikka, M., Rauvala, H., et al. (2004). Vascular endothelial growth factor C is required for sprouting of the first lymphatic vessels from embryonic veins. Nat Immunol 5, 74-80.

Kuchler, A. M., Gjini, E., Peterson-Maduro, J., Cancilla, B., Wolburg, H., and Schulte-Merker, S. (2006). Development of the zebrafish lymphatic system requires VEGFC signaling. Curr Biol 16, 1244-1248.

Levine, A. J., Munoz-Sanjuan, I., Bell, E., North, A. J., and Brivanlou, A. R. (2003). Fluorescent labeling of endothelial cells allows in vivo, continuous characterization of the vascular development of *Xenopus laevis*. Dev Biol 254, 50-67.

Makinen, T., Jussila, L., Veikkola, T., Karpanen, T., Ketumen, M. I., Pulkkanen, K. J., Kauppinen, R., Jackson, D. G., Kubo, H., Nishikawa, S., et al. (2001). Inhibition of lymphangiogenesis with resulting lymphedema in transgenic mice expressing soluble VEGF receptor-3. Nat Med 7, 199-205.

Mandriota, S. J., Jussila, L., Jeltsch, M., Compagni, A., Battens, D., Prevo, R., Banerji, S., Huarte, J., Montesano, R., Jackson. D. G., et al. (2001). Vascular endothelial growth factor-C-mediated lymphangiogenesis promotes tumour metastasis. Embo J 20, 672-682.

Min., J., Kyung Kim, Y., Cipriani, P. G., Kang, M., Khersonsky, S. M., Walsh, D. P., Lee, J. Y., Niessen, S., Yates, J. R., 3rd. Gunsalus, K., et al. (2007). Forward chemical genetic approach identifies new role for GAPDH in insulin signaling. Nat Chem Biol 3, 55-59.

Nieuwkoop, P. D., and Faber, J. (1994). Normal table of *Xenopus laevis* (Daudin): a systematical and chronological survey of the development from the fertilized egg till the end of metamorphosis (New York & London, Garland Publishing, Inc.).

Ny, A., Koch, M., Schneider, M., Neven, E., Tong, R. T., Maity. S., Fischer, C., Plaisance, S., Lambrechts, D., Heligon, C., et al. (2005). A genetic *Xenopus laevis* tadpole model to study lymphangiogenesis. Nat Med 11, 998-1004.

Pang, C., Seng, W. L., Semino, C., and McGrath, P. (2002). Zebrafish: a preclinical model for drug screening, Assay Drug Dev Technol 1, 41-48.

Pepper, M. S., Tille, J. C., Nisato, R., and Skobe, M. (2003). Lymphangiogenesis and tumor metastasis. Cell Tissue Res 314, 167-177.

Petrova, T. V., Makinen, T. Makela, T. P., Saarela, J., Virtanen, I., Ferrell, R. E., Finegold, D. N., Kerjaschki, D., Yla-Herttuala, S., and Alitalo, K. (2002). Lymphatic endothelial reprogramming of vascular endothelial cells by the Prox-1 homeobox transcription factor. Embo J 21, 4593-4599.

Pyriochou A., Beis, D., Koika, V., Potytarchou, C., Papadimitriou, E., Zhou, Z., and Papapetropoulos, A. (2006). Soluble guanylyl cyclase activation promotes angiogenesis. J Pharmacol Exp Ther 319, 663-671.

Raciti, D., Reggiani, L., Geffers, L., Jiang, Q., Bacchion, F., Subrizi, A. E., Clements, D., Tindal, C., Davidson. D. R., Kaissling, B., et al. (2008). Organization of the pronephric kidney revealed by large-scale gene expression mapping. Genome Biol. 9, R84.

Ram, C. V. (2006). Hypertension, possible vascular protection and lercanidipine. Expert Rev Cardiovasc Ther 4, 783-788.

Rickardson, L., Fryknas, M., Haglund, C., Lovborg, H., Nygren, P., Gustafsson, M. G., Isaksson, A., and Larsson, R. (2006). Screening of an annotated compound library for drug activity in a resistant myeloma cell line. Cancer Chemother Pharmacol 58, 749-758.

Roesli C., Mumprecht, V., Neri, D., and Detmar, M. (2008). Identification of the surface-accessible, lineage-specific vascular proteome by two-dimensional peptide mapping. FASEB J 22, 1933-1944.

Root, D. E. Flaherty, S. P. Kelley, B. P., and Stockwell, B. R. (2003). Biological mechanism profiling using an annotated compound library. Chem Biol 10, 881-892.

Saulnier, D. M., Ghanbari, H., and Brändli, A. W. (2002). Essential function of Wnt-4 for tubulogenesis in the *Xenopus* pronephric kidney. Dev Biol 248, 13-28.

Seiffert, D., Bradley, J. D., Rominger, C. M., Rominger, D. H., Yang, F., Meredith, J. E., Jr., Wang, Q., Roach, A. H., Thompson, L. A., Spitz, S. M., et al. (2000). Presenilin-1 and -2 are molecular targets for gamma-secretase inhibitors. J Biol Chem 275, 34086-34091.

Serbedzija, G. N., Flynn, E., and Willett, C. E. (1999). Zebrafish angiogenesis: a new model for drug screening. Angiogenesis 3, 353-359.

Skobe, Hawighorst, T., Jackson, D. G., Prevo, R., Janes, L., Velasco, P., Riccardi, L., Alitalo, K., Claffey, K., and Detmar, M. (2001). Induction of tumor lymphangiogenesis by VEGF-C promotes breast cancer metastasis. Nat Med 7, 192-198.

Stacker, S. A., Caesar, C., Baldwin, M. E., Thornton, G. E., Williams, R. A., Prevo, R., Jackson, D. G., Nishikawa, S., Kubo, H., and Achen, M. G. (2001). VEGF-D promotes the metastatic spread of tumor cells via the lymphatics. Nat Med 7, 186-191.

Stockwell, B. R. (2000). Chemical genetics: ligand-based discovery of gene function. Nat Rev Genet 1, 116-125.

Tobler, N. E., and Detmar. M. (2006). Tumor and lymph node lymphangiogenesis—impact on cancer metastasis. J Leukoc Biol 80, 691-696.

Tomlinson, M. L., Field, R. A., and Wheeler, G. N. (2005). *Xenopus* as a model organism in developmental chemical genetic screens. Mol Biosyst 1, 223-228.

Tran, T. C., Sneed, B., Haider, J., Blavo, D., White, A., Aiyejorun, T., Baranowski, T. C., Rubinstein, A. L., Doan. T. N., Dingledine, R., et al. (2007). Automated, quantitative screening assay for antiangiogenic compounds using transgenic zebrafish. Cancer Res 67, 11386-11392.

Yaniv, K., Isogai, S., Castranova, D., Dye, L., Hitomi, J., and Weinstein, B. M. (2006). Live imaging of lymphatic development in the zebrafish, Nat Med 12, 711-716.

Zon, L. I., and Peterson, R. T. (2005). In vivo drug discovery in the zebrafish. Nat Rev Drug. Discov 4, 35-44.

TABLE 1

Summary of the results from the phenotypic chemical library screen of Xenopus embryos

| Phenotype | Number of compounds | % of compounds tested |
|---|---|---|
| Normal embryogenesis | 1116 | 91.1 |
| Abnormal embryogenesis | 114 | 8.9 |
| Total | 1280 | 100.0 |
| Phenotype classes | | |
| Cytoxicity | 32 | 2.5 |
| Lethality | 18 | 1.4 |
| Edema formation | 48 | 3.7 |
| Pigmentation defects | 10 | 0.8 |
| Other defects | 6 | 0.5 |
| Total | 114 | 8.9 |

TABLE 2

Compilation of 32 compounds causing cytotoxicity in Xenopus embryos

| Name | Secondary Name | Class | Enzyme | Action | Selectivity | Lethality (NF) |
|---|---|---|---|---|---|---|
| Niclosamide | 2',5'-Dichloro-4'-nitrosalicylanilide | Antibiotic | | | Protonophore | 32 |
| beta-Lapachone | | Apoptosis | | Activator | | 32 |
| Z-L-Phe chloromethyl ketone | N-Carbobenzyloxy-L-phenylalanyl chloromethyl ketone; ZPCK | Biochemistry | Enzyme | Inhibitor | Chymotrypsin A-gamma | 32 |
| (R)-(+)-WIN 55,212-2 mesylate | (R)-(+)-[2,3-Dihydro-5-methyl-3[(morpholinyl)methyl]pyrrolo[1,2,3-de]-1,4-benzoxazinyl]-(1-naphthalenyl)methanone mesylate | Cannabinoid | | Agonist | | 32 |
| Bay 11-7085 | (E)-3-(4-t-Butylphenylsulfortyl)-2-propenenitrile | Cell Cycle | | Inhibitor | IkB-alpha | 32 |
| Rotenone | | Cell Stress | | Modulator | Mitochondria | 32 |
| 2-(alpha-Naphthoyl)ethyltrimethylammonium iodide | alpha-NETA | Cholinergic | Enzyme | Inhibitor | Choline Acetyltransferase | 32 |
| 5-Nitro-2-(3-phenylpropylamino) benzoic acid | NPPB | Cl— Channel | | Blocker | | 32 |
| Brefeldin A front Penicillium brefeldianum | BFA; Ascotoxin, Cyanein | Cytoskeleton and ECM | | Inhibitor | Golgi apparatus | 33/34 |
| Fluspirilene | R 6218 | Dopamine | | Antagonist | D2/D1 | 32 |
| Farnesylthiosalicylic acid | FTS | G protein | Enzyme | Antagonist | Ras | 32 |
| Calcimycin | A23187; Calcium ionophore A23187 | Intracellular Calcium | | | Ca2+ | 32 |
| Thapsigargin | | Intracellular Calcium | Enzyme | Releaser | | 32 |
| Sanguinarine chloride | 13-Methyl-[1,3]benzodioxolo[5,6-c]-1,3-dioxolo[4,5-i]phenanthridinium chloride | Ion Pump | | Inhibitor | Na+/K+ ATPase | 32 |
| Ebselen | 2-Phenyl-1,2-benzisoselenazol-3(2H)-one | Leukotriene | Enzyme | Inhibitor | Lipoxygenases/glutathione S-transferase | 32 |
| SR 2640 | 2-[[3-(2-Quinolinylmethoxy)phenyl]amino]-benzoic acid; QMPB | Leukotriene | | Antagonist | CysLT1 | 32 |
| D-609 potassium | Carbonodithioic acid, O-(octahydro-4,7-methano-1H-inden-5-yl) ester potassium | Lipid | Enzyme | Inhibitor | PIPLC | 33/34 |

TABLE 2-continued

Compilation of 32 compounds causing cytotoxicity in Xenopus embryos

| Name | Secondary Name | Class | Enzyme | Action | Selectivity | Lethality (NF) |
|---|---|---|---|---|---|---|
| MJ33 | 1-Hexadecyl-3-(trifluoroethyl)-sn-glycero-2-phosphomethanol lithium | Lipid | Enzyme | Inhibitor | PLA2 | 32 |
| Ro 41-0960 | 2'-Fluoro-3,4-dihydroxy-5-nitrobenzophenone | Neurotransmission | Enzyme | Inhibitor | COMT | 33/34 |
| Cantharidic Acid | | Phosphorylation | Enzyme | Inhibitor | PP1/PP2A | 32 |
| Cantharidin | Cantharidine | Phosphorylation | Enzyme | Inhibitor | PP2A | 32 |
| Dequalinium analog, C-14 linker | C14 Linker; DECA-14; Quinolinium | Phosphorylation | Enzyme | Inhibitor | PKC-alpha | 32 |
| Palmitoyl-DL-Carnitine chloride | | Phosphorylation | Enzyme | Modulator | PKC | 32 |
| Phorbol 12-myristate 13-acetate | PMA | Phosphorylation | Enzyme | Activator | PKC | 32 |
| rac-2-Ethoxy-3-hexadecanamido-1-propylphosphocholine | | Phosphorylation | Enzyme | Inhibitor | PKC | 32 |
| rac-2-Ethoxy-3-octadecanamido-1-propylphospocholine | | Phosphorylation | Enzyme | Inhibitor | PKC | 32 |
| Rottlerin | Mallotoxin | Phosphorylation | Enzyme | Inhibitor | PKC/CaM Kinase III | 32 |
| Tyrphostin A9 | [[3,5-bis(1,1-Dimethylethyl)-4-hydroxyphenyl]methylene]-propanedinitrile | Phosphorylation | Enzyme | Inhibitor | PDGFR | 32 |
| Tyrphostin AG 879 | alpha-cyano-(3,5-di-t-butyl-4-hydroxy)thiocinnamide | Phosphorylation | Enzyme | Inhibitor | TrkA | 32 |
| Wortmannin from Penicillium funiculosum | | Phosphorylation | Enzyme | Inhibitor | PI3K | 33/34 |
| L-655,240 | 3-[1-(4-Chlorobenzyl)-5-fluoro-3-methyl-indol-2-yl]-2,2-dirriethyl propanoic acid | Thromboxane | | Antagonist | TXA2 | 32 |
| GW7647 | 2-(4-(2-(1-Cyclohexanebutyl)-3-cyclohexylureido)ethyl)phenylthio)-2-methylpropionic acid | Transcription | | Agonist | PPAR-alpha | 32 |

TABLE 3

Compilation of 18 compounds causing lethality in Xenopus embryos

| Name | Secondary Name | Class | Enzyme | Action | Selectivity | Lethality (NF) |
|---|---|---|---|---|---|---|
| FPL 64176 | 2,5-Dimethyl-4-[2-(phenylmethyl)benzoyl]-1H-pyrrole-3-carboxylic acid methyl ester | Ca2+ Channel | | Activator | L-type | 40 |
| Nitrendipine | 1,4-Dihydro-2,6-dimethyl-4-(3-nitrophenyl)-3,5-pyridinecarboxylic acid ethyl methyl ester | Ca2+ Channel | | Antagonist | L-type | 45 |
| TG003 | (Z)-1-(3-Ethyl-5-methoxy-2,3-dihydrobenzothiazol-2-ylidene)-propan-2-one | Cell Cycle | Enzyme | Inhibitor | Clk | 40 |
| Ivermectin | MK-933 | Cholinergic | | Modulator | alpha7 nACh | 41/42 |
| Loratadine | 4-(8-chloro-5,6-dihydro-11H-benzo[5,6]cyclohepta[1,2-bipyridin-11-ylidene-l-piperidinecarboxylic acid ethyl ester | Histamine | | Antagonist | H1 | 45 |

TABLE 3-continued

Compilation of 18 compounds causing lethality in Xenopus embryos

| Name | Secondary Name | Class | Enzyme | Action | Selectivity | Lethality (NF) |
|---|---|---|---|---|---|---|
| (R,R)-cis-Diethyl tetrahydro-2,8-chrysenediol | (5R, 11R)-5,11-Diethyl-5,6,11,12-tetrahydro-2,8-chrysenediol | Hormone | | Antagonist | ER-beta | 41 |
| Calmidazolium chloride | R 24571 chloride | Intracellular Calcium | Enzyme | Inhibitor | Ca2+ ATPase | 37/38 |
| MK-886 | 3[3-tert-Butylthio-1-(4-chlorobenzyl)-5-isopropyl-1H-indol-2-yl]-2,2-dimethylpropionic acid, sodium salt | Leukotriene | | Inhibitor | | 39 |
| ET-18-OCH3 | 3,5,9-Trioxa-4-phosphaheptacosan-1-aminium | Lipid | Enzyme | Inhibitor | PIPLC | 37/38 |
| L-162,313 | (5,7-dimethyl-2-ethyl-3-[[4-[2(n-butyloxycarbonylsulfonamido)-5-isobutyl-3-thienyl]phenyl]methyl] imidazo[4,5,6]pyridine | Neurotransmission | | Agonist | AT1 | 45 |
| N-Oleoyldopamine | OLDA | Neurotransmission | | Ligand | CB1 | 41 |
| DL-Stearoylcarnitine chloride | | Phosphorylation | Enzyme | Inhibitor | PKC | 41 |
| Indirubin-3'-oxime | Indirubin-3'-monoxime | Phosphorylation | Enzyme | Inhibitor | CDK | 45 |
| NSC 95397 | 2,3-bis[(2-Hydroxyethyl)thio]-1,4-naphthoquinone | Phosphorylation | Enzyme | Inhibitor | Cdc25 | 40 |
| Purvalanol A | NG-60 | Phosphorylation | Enzyme | Inhibitor | CDK | 41/42 |
| SP600125 | Anthrapyrazolone; 1,9-Pyrazoloanthrone | Phosphorylation | Enzyme | Inhibitor | c-JNK | 41 |
| SU 5416 | 1,3-Dihydro-3-[(3,5-dimethyl-1H-pyrrol-2-yl)methylene]-2H-indol-2-one | Phosphorylation | | Inhibitor | VEGER PTK | 37/38 |
| (±)-Ibuprofen | alpha-Methyl-4-(isobutyl)phenylacetic acid | Prostaglandin | Enzyme | Inhibitor | COX | 45 |

TABLE 4

Compilation of 48 compounds causing edema in Xenopus embryos

| Name | Secondary Name | Class | Enzyme | Action | Selectivity | Onset (NF) | Lethality (NF) |
|---|---|---|---|---|---|---|---|
| 1,3-Diethyl-8-phenylxanthine | DPX | Adenosine | | Antagonist | A1 | 41/42 | 45 |
| 7-Chloro-4-hydroxy-2-phenyl-1,8-naphthyridine | | Adenosine | | Antagonist | A1 | 39 | 39 |
| CGS-15943 | 9-Chloro-2-(2-furyl)[1,2,4]triazolo[1,5-c]quinazolin-5-amine | Adenosine | | Antagonist | A1 | 41/42 | 46 |
| L-765,314 | (2S)-4-(4-Amino-6,7-dimethoxy-2-quinazolinyl)-2-[[(1,1-Dimethylethyl)amino]carbonyl]-1-piperazinecarboxylic acid, phenylmethyl ester | Adrenoceptor | | Antagonist | alpha-1B | 41/42 | — |
| Mevastatin | Compactin | Antibiotic | Enzyme | Inhibitor | Ras, Rho | 35/36 | 45 |
| 4-Amino-1,8-naphthalimide | | Apoptosis | Enzyme | Inhibitor | PARP | 41/42 | — |
| Retinoic acid | Vitamin A acid | Apoptosis | Enzyme | Activator | | 39 | 40 |
| 1,10-Phenanthroline monohydrate | o-Phenanthroline monohydrate | Biochemistry | Enzyme | Inhibitor | Metalloprotease | 39/40 | 46 |
| Felodipine | Plendil | Ca2+ Channel | | Blocker | L-type | 41/42 | 45 |
| MRS 1845 | N-Propargylnitrendipene | Ca2+ Channel | | Inhibitor | SOC | 41/42 | 45 |
| Nicardipine hydrochloride | YC-93 hydrochloride | Ca2+ Channel | | Antagonist | L-type | 41/42 | 45 |
| Nifedipine | | Ca2+ Channel | | Antagonist | L-type | 41/42 | 46 |

TABLE 4-continued

Compilation of 48 compounds causing edema in Xenopus embryos

| Name | Secondary Name | Class | Enzyme | Action | Selectivity | Onset (NF) | Lethality (NF) |
|---|---|---|---|---|---|---|---|
| Nimodipine | 1,4-Dihydro-2,6-dimethyl-4-(3-nitrophenyl)-3,5-pyridinecarboxylic acid 2-methoxyethyl 1-methylethyl ester | Ca2+ Channel | | Antagonist | L-type | 41/42 | 41/42 |
| SKF 96365 | 1-(beta-[3-(4-Methoxyphenyl)propoxy]-4-methoxyphenethyl)-1H-imidazole hydrochloride | Ca2+ Channel | | Inhibitor | | 39 | 41/42 |
| (±)alpha-Lipoic Acid | (±)-1,2-Dithiolane-3-pentanoic acid | Cell Stress | Enzyme | Coenzyme | Pyruvate dehydrogenase | 39 | 45 |
| Forskolin | | Cyclic Nucleotides | Enzyme | Activator | Adenylate cyclase | 39/40 | 41/42 |
| YC-1 | 3-(5'-Hydroxymethyl-2'-fulyl)-1-benzyl indazole | Cyclic Nucleotides | Enzyme | Activator | Guanylyl cyclase | 45 | — |
| Zardaverine | 6-(4-Difluoromethoxy-3-methoxyphenyl)-3(2H)-pyridazinone | Cyclic Nucleotides | Enzyme | Inhibitor | PDE III/PDE IV | 39/40 | 43 |
| Nocodazole | R 17934 | Cytoskeleton and ECM | | Inhibitor | beta-tubulin | 33/34 | 33/34 |
| Podophyllotoxin | | Cytoskeleton and ECM | | Inhibitor | | 39/40 | 41/42 |
| GBR-12909 dihydrochloride | 1-[2-[bis(4-Fluorophenyl)methoxy]ethyl]-4-[3-phenylpropyl]piperazine dihydrochloride | Dopamine | | Inhibitor | Reuptake | 45 | — |
| N-(p-Isothiocyanatophenethyl)spiperone hydrochloride | NIPS hydrochloride | Dopamine | | Antagonist | D2 | 45 | — |
| Pimozide | | Dopamine | | Antagonist | D2 | 41/42 | 45 |
| Sobuzoxane | 4,4'-(1,2-Ethanediyl)bis(1-isobutoxycarbonyloxymethyl-2,6-piperazinedione) | Gene Regulation | Enzyme | Inhibitor | Topo II | 41/42 | 47 |
| Riluzole | 2-Amino-6-(trifluoromethoxy)-benzothiazole | Glutamate | | Antagonist | Release | 45 | — |
| Clemastine fumarate | | Histamine | | Antagonist | H1 | 45 | — |
| 2-methoxyestradiol | 2-Hydroxyestradiol 2-methyl ether | Hormone | | Metabolite | Estrogen | 33/34 | 33/34 |
| beta-Estradiol | Dihydrofolliculin | Hormone | | | Estrogen | 42 | 45 |
| Dequalinium dichloride | 1,1'-Decamethylenebis(4-aminoquinaldinium) dichloride | K+ Channel | | Blocker | | 39 | 39 |
| 7-Cyclopentyl-5-(4-phenoxy)phenyl-7H-pyrrolo[2,3-d]pyrimidin-4-ylamine | | Phosphorylation | Enzyme | Inhibitor | Ick | 41/42 | 45 |
| Cyclosporin A | Antibiotic S 7481F1 | Phosphorylation | Enzyme | Inhibitor | Calcineurin phosphatase | 41/42 | — |
| Diacylglycerol kinase inhibitor I | R 59022 | Phosphorylation | Enzyme | Inhibitor | Diacylglycerol kinase | 45 | — |
| Diacylglycerol Kinase Inhibitor II | R59949 | Phosphorylation | Enzyme | Inhibitor | Diacylglycerol kinase | 41/42 | — |
| Genistein | 5,7-Dihydroxy-3-(4-hydroxyphenyl)-4H-1-benzopyran-4-one | Phosphorylation | Enzyme | Inhibitor | Tyrosine kinase | 35/36 | 46 |
| GW2974 | N4-(1-Benzyl-1H-indazol-5-yl)-N6,N6-dimethyl-pyrido[3,4-d]pyrimidine4,6-diamine | Phosphorylation | Enzyme | Inhibitor | EGFR/ErbB-2 | 41/42 | 47 |
| GW5074 | 3-(3, 5-Dibromo-4-hydroxybenzylidine-5-iodo-1,3-dihydro-indol-2-one) | Phosphorylation | Enzyme | Inhibitor | Raf1 kinase | 33/34 | 41/42 |
| IC 261 | 1,3-Dihydro-3-[(2,4,6-trimethoxyphenyl)methylene]-2H-indol-2-one | Phosphorylation | Enzyme | Inhibitor | CK-1delta/epsilon | 35/36 | 41/42 |
| Kenpaullone | NSC 664704 | Phosphorylation | Enzyme | Inhibitor | CDK1, CDK2, CDK5 | 45 | — |

TABLE 4-continued

Compilation of 48 compounds causing edema in Xenopus embryos

| Name | Secondary Name | Class | Enzyme | Action | Selectivity | Onset (NF) | Lethality (NF) |
|---|---|---|---|---|---|---|---|
| SU 4312 | 3-(4-Dimethylaminobenzylidenyl)-2-indolinone | Phosphorylation | Enzyme | Inhibitor | KDR | 45 | — |
| SU 6656 | 2,3-Dihydro-N,N-dimethyl-2-oxo-3-[(4,5,6,7-tetrahydro-1H-indol-2-yl)methylene]-1H-indole-5-sulfonamide | Phosphorylation | Enzyme | Inhibitor | Src family kinase | 39/40 | 46 |
| Tyrphostin AG 1478 | N-(3-Chlorophenyl)-6,7-dimethoxy-4-quinazolinamine | Phosphorylation | Enzyme | Inhibitor | EGFR | 45 | 46 |
| Tyrphostin AG 494 | N-Phenyl-3,4-dihydroxybenzylidenecyanoacetamide | Phosphorylation | Enzyme | Inhibitor | EGFR | 39 | 40 |
| Meclofenamic acid sodium | 2-([2,6-Dichloro-3-methylphenyl]amino)benzoic acid sodium | Prostaglandin | Enzyme | Inhibitor | COX/5-Lipoxygenase | 35/36 | 41/42 |
| Amperozide hydrochloride | 4-[4,4-bis(4-Fluorophenyl)butyl]-N-ethyl-1-piperazinecarboxamide hydrochloride | Serotonin | | Ligand | | 41/42 | — |
| Ritanserin | 6-[2-[4-bis(4-Fluorophenyl)methylene]-1-piperidinyl]-ethyl]-7-methyl-5H-thiazolo[3,2-a]pyrimidin-5-one | Serotonin | | Antagonist | 5-HT2/5-HT1C | 41/42 | — |
| 13-cis-retinoic acid | Isotretinoin | Transcription | | Regulator | RAR-alpha, beta | 41/42 | 46 |
| 6(5H-Phenanthridinone | | Transcription | Enzyme | Inhibitor | PARP | 45 | 47 |
| TTNPB | Arotinoid acid | Transcription | | Ligand | RAR-alpha, beta, gamma | 39 | 45 |

TABLE 5

Compilation of 10 compounds causing pigmentation defects in Xenopus embryos.

| Name | Secondary Name | Class | Enzyme | Action | Selectivity | Phenotypes | Onset (NF) | Lethality (NF) |
|---|---|---|---|---|---|---|---|---|
| (-)-Ephedrine hemisulfate | | Adrenoceptor | | Activator | | Lack of skin pigmentation | 33/34 | 41/42 |
| Nalidixic acid sodium | 1-Ethyl-1,4-dihydro-7-methyl-4-oxo-1,8-naphthyridine-3-carboxylic acid sodium | Antibiotic | Enzyme | Inhibitor | DNA Gyrase | Silvery-colored embryos | 47 | — |
| Caffeic acid phenethyl ester | CAPE | Cell Cycle | | Inhibitor | NFkB | Lack of skin pigmentation | 33/34 | 39 |
| 1-Phenyl-3-(2-thiazolyl)-2-thiourea | | Dopamine | Enzyme | Inhibitor | beta-Hydroxylase | Reduced eye & skin pigmentation | 33/34 | — |
| Amfonelic acid | 7-Benzyl-1-ethyl-1,4-dihydro-4-oxo-1,8-naphthyridine-3-carboxylic acid | Dopamine | | Modulator | | Reduced eye & skin pigmentation | 33/34 | — |
| Apomorphine hydrochloride hemihydrate | 10,11-Dihydroxyaporphine hydrochloride hemihydrate | Dopamine | | Agonist | | Reduced eye & skin pigmentation | 33/34 | — |
| R(-)-N-Allylnorapomorphine hydrobromide | | Dopamine | | Agonist | | Lack of skin pigmentation; Delayed embryogenesis; Paralyzed embryos | 33/34 | 40 |
| R(-)-Propylnorapomorphine hydrochloride | R(-)-NPA hydrochloride | Dopamine | | Agonist | D2 | Reduced skin pigmentation | 33/34 | — |

TABLE 5-continued

Compilation of 10 compounds causing pigmentation defects in Xenopus embryos.

| Name | Secondary Name | Class | Enzyme | Action | Selectivity | Phenotypes | Onset (NF) | Lethality (NF) |
|---|---|---|---|---|---|---|---|---|
| Spiroxatrine | R 5188 | Serotonin | | Agonist | 5-HT1A | Increased skin pigmentation | 45 | — |
| WIN 62,577 | 17-beta-Hydroxy-17-alpha-ethynyl-delta-4-androstano(3,2-b)pyrimido(1,2-a)benzimidazole | Tachykinin | | Antagonist | NK1 | Reduced eye & skin pigmentation | 33/34 | 42 |

TABLE 6

Compilation of 6 compounds causing other phenotypic defects in Xenopus embryos.

| Name | Secondary Name | Class | Enzyme | Action | Selectivity | Phenotypes | Onset (NF) | Lethality (NF) |
|---|---|---|---|---|---|---|---|---|
| (S)-(+)-Camptothecin | | Apoptosis | Enzyme | Inhibitor | Topo1 | Worm-like, crippled embryos; Tremoring embryos; Very small eyes | 39 | 41/42 |
| 2,3-Dimethoxy-1,4-naphthoquinone | DMNQ | Cell Stress | | Modulator | | Brown discoloration; Tremoring embryos | 41 | 42 |
| SB 205384 | 4-Amino-7-hydroxy-2-methyl-5,6,7,8-tetrahydrobenzo[b]thieno[2,3-b]pyridine-3-carboxylic acid but-2-ynyl ester | GABA | | Modulator | GABA-A | Brown discoloration; Delayed embryogenesis | 40 | 46 |
| trans-Dehydroandrosterone | 5-Androsten-3beta.ol-17-one; DHEA | Hormone | | | Aldosterone | Brown discoloration; Tremoring embryos | 41/42 | — |
| 3-Aminopropionitrile fumarate | | Multi-Drug Resistance | Enzyme | Substrate | CYP450 | Swollen vacuoles in the tail's notochord | 46 | — |
| Diphenyleneiodonium chloride | [1,1'-Biphenyl]-2,2'-diyiodonium chloride | Nitric Oxide | Enzyme | Inhibitor | eNOS | Brown discoloration; Tremoring embryos | 41 | 42 |

TABLE 7

Bioactive pharmacological classes by phenotype

| | Screen | | Cytotoxicity | | Lethality | | Edema | | Pigmentation | | Other | |
|---|---|---|---|---|---|---|---|---|---|---|---|---|
| Class[+] | Total agents | Total active | Active agents | % total | Active agents | % total | Active agents | % total | Active agents | % total | Active agents | % total |
| Adenosine | 55 | 3 | | | | | 3 | 5.5 | | | | |
| Adrenoreceptor | 104 | 2 | | | | | 1 | 1.0 | 1 | 1.0 | | |
| Antibiotic | 28 | 3 | 1 | 3.6 | | | 1 | 3.6 | 1 | 3.6 | | |
| Apoptosis | 12 | 4 | 1 | 8.3 | | | 2 | 16.7 | | | 1 | 8.3 |
| Biochiemistry | 46 | 2 | 1 | 2.2 | | | 1 | 2.2 | | | | |
| $Ca^{2+}$ Channel | 18 | 8 | | | 2 | 11.1 | 6 | 33.3 | | | | |
| Cannabinoid | 6 | 1 | 1 | 16.7 | | | | | | | | |
| Cell cycle | 15 | 3 | 1 | 6.7 | 1 | 6.7 | | | 1 | 6.7 | | |
| Cell stress | 19 | 3 | 1 | 5.3 | | | 1 | 5.3 | | | 1 | 5.3 |
| Cholinergic | 77 | 2 | 1 | 1.3 | 1 | 1.3 | | | | | | |
| $Cl^-$ Channel | 3 | 1 | 1 | 33.3 | | | | | | | | |
| Cyclic nucleotides | 31 | 3 | | | | | 3 | 9.7 | | | | |
| Cytoskeleton & ECM | 10 | 3 | 1 | 10.0 | | | 2 | 20.0 | | | | |
| Dopamine | 114 | 9 | 1 | 0.9 | | | 3 | 2.6 | 5 | 4.4 | | |
| G protein | 4 | 1 | 1 | 25.0 | | | | | | | | |
| GABA | 42 | 1 | | | | | | | | | 1 | 2.4 |
| Gene regulation | 1 | 1 | | | | | 1 | 100.0 | | | | |
| Glutamate | 88 | 1 | | | | | 1 | 1.1 | | | | |
| Histamine | 31 | 2 | | | 1 | 3.2 | 1. | 3.2 | | | | |
| Hormone | 34 | 4 | | | 1 | 2.9 | 2 | 5.9 | | | 1 | 2.9 |
| Intracellular calcium | 8 | 3 | 2 | 25.0 | 1 | 12.5 | | | | | | |

TABLE 7-continued

Bioactive pharmacological classes by phenotype

| | Screen | | Cytotoxicity | | Lethality | | Edema | | Pigmentation | | Other | |
|---|---|---|---|---|---|---|---|---|---|---|---|---|
| Class[+] | Total agents | Total active | Active agents | % total | Active agents | % total | Active agents | % total | Active agents | % total | Active agents | % total |
| Ion pump | 17 | 1 | 1 | 5.9 | | | | | | | | |
| K[+] Channel | 19 | 1 | | | | | 1 | 5.3 | | | | |
| Leukotriene | 10 | 3 | 2 | 20.0 | 1 | 10.0 | | | | | | |
| Lipid | 10 | 3 | 2 | 20.0 | 1 | 10.0 | | | | | | |
| Multi-drug resistance | 12 | 1 | | | | | | | | | 1 | 8.3 |
| Neurotransmission | 46 | 3 | 1 | 2.2 | 2 | 4.3 | | | | | | |
| Nitric oxide | 37 | 1 | | | | | | | | | 1 | 2.7 |
| Phosphorylation | 92 | 30 | 11 | 12.0 | 6 | 5.5 | 13 | 14.1 | | | | |
| Prostaglandin | 24 | 2 | | | 1 | 4.2 | 1 | 4.2 | | | | |
| Serotonin | 87 | 3 | | | | | 2 | 2.3 | 1 | 1.1 | | |
| Tachykinin | 5 | 1 | | | | | | | 1 | 20 | | |
| Thromboxane | 2 | 1 | 1 | 50.0 | | | | | | | | |
| Transcription | 12 | 4 | 1 | 8.3 | | | 3 | 25.0 | | | | |
| Entire Screen | 1280 | 114 | 32 | 2.5* | 18 | 1.4* | 48 | 3.8* | 10 | 0.8* | 6 | 0.5* |

[+]Includes only bioactive classes.
*Frequency of whole screen.

TABLE 8

Phenotypic classification of edema-inducing compounds

| Phenotype class | Compound name | Pharmacological class | Selectivity | Cerebral | Periocular | Pericordial | Type of edema Ventral | Proctodeal | Pronephric | Tail tip | Cardiac phenotype | Lymph heart enlargement | Lethality |
|---|---|---|---|---|---|---|---|---|---|---|---|---|---|
| A | 1,3-Diethyl-8-phenylxanthine | Adenosine | A1 | | | 41/42 | 41/42 | | | | | | 45 |
| | CGS -15943 | Adenosine | A1 | | | 41/42 | 45 | | | | | | 46 |
| | Mevastatin | Antibiotic | Ras, Rho | | | 35/36 | 41/42 | | | | | | 45 |
| | 1,10-Phenenthroline monohydrate | Biochemistry | Metalloprotease | | | 39/40 | 41/42 | | | | | | 46 |
| | Felodipine | Ca2+ Channel | L-type | | | 41/42 | 41/42 | | 45 | | | | 45 |
| | MRS 1845 | Ca2+ Channel | SOC | | | 41/42 | 41/42 | | 41/42 | | | | 45 |
| | Nicardipine hydrochloride | Ca2+ Channel | L-type | | | 41/42 | 41/42 | | 41/42 | | | | 45 |
| | Nifedipine | Ca2+ Channel | L-type | | 41/42 | 41/42 | 45 | | | | | | 46 |
| | Nimodipine | Ca2+ Channel | L-type | | | 41/42 | 41/42‡ | | | | 41/42¶ | | 41/42 |
| | SKF 96365 | Ca2+ Channel | L-type | | | 39 | 40 | 40 | | | | | 41/42 |
| | Forskolin | Cyclic Nucleotides | Adenylate cyclase | | | 39 | 39 | 39 | | | | | 41/42 |
| | Pimozide | Dopamine | D2 | | | 41/42 | 41/42 | | 41/42 | | 41/42¶ | | 45 |
| | Clemastine fumarate | Histamine | H1 | | 46 | 46 | 45 | | | | | | |
| | GW2974 | Phosphorylation | EGFR/ErbB2 | | 41/42 | 41/42 | 41/42 | | | | | | 47 |
| | Amperozide hydrochloride | Serotonin | | | 45 | 45 | 45 | | | | | | |
| | 6(5H)-Phenanthridinone | Transcription | PARP | | 45 | 45 | | | | | | | 47 |
| | L-765,314 | Adrenoceptor | alpha-1B | | 41/42 # | | | | | | | | |
| B | YC -1 | Cyclic Nucleotides | Guanylyl cyclase | | 45 | | 45 | | | | | | |
| | GBR-12909 dihydrochloride | Dopamine | Reuptake | | 45 | | 45 | | 45 | | | | |
| | N-(p-Isothiocyanatophenethyl) spiperone hydrochloride | Dopamine | D2 | | 45 | | 45 | | | | | | |
| | Riluzole | Glutamate | Release | | 45 | | 45 | | 45 | | | | 45 |
| | beta-Estradiol | Hormone | Estrogen | | 42 # | | | | | | | | |
| | Cyclosporin A | Phosphorylation | Calcineurin phosphatase | | 45 | | 45 | | 41/42 | | | | |
| | Diacylglycerol Kinase inhibitor I | Phosphorylation | Diacyglycerol kinase | | 45 | | 45 | | 45 | | | | |
| | Diacylglycerol Kinase Inhibitor II | Phosphorylation | Diacyglycerol kinase | | 46 | | 41/42 | | | | | | |
| | Kenpaullone | Phosphorylation | CDK1, CDK2, CDK5 | | 45 | | 45 | | | | | | |
| | SU 4312 | Phosphorylation | KDR | | 45 | | 45 | | 45 | | | | |
| | Ritanserin | Serotonin | 5-HT2/5-HT1C | | 41/42 | | 41/42 | | 45 | | | | |
| C | Naphthyridine | Adenosine | A1 | | | 39 | | | | | | | 39 |
| | (±)-alpha-Lipoic Acid | Cell stress | | | | 39 | | | 42 | | | | 45 |
| | Zardaverine | Cyclic Nucleotides | PDE III/PDE IV | | | 39/40 | | | 41/42 | | | | 43 |
| | Nocodazole | Cyleskeleton and ECM | beta-tubulin | | | 33/34 | | | | | | | 33/34 |
| | Podophyllotoxin | Cyloskeleton and ECM | | | | 39/40 | | | | | | | 41/42 |
| | 2-methoxyestradiol | Hormone | Estrogen | | | 33/34 | | | | | | | 33/34 |
| | Dequalinium dichloride | K+ Channel | | | | 39 | | | | | | | 39 |
| | 7-Cyclo | Phosphorylation | lck | | | 41/42 | 41/42 | | 41/42 | | | | 45 |
| | GW5074 | Phosphorylation | Raf 1 kinase | | | 33/34 | | | | | | | 41/42 |
| | Meclofenamic acid sodium | Prostaglandin | COX/5-Lipoxygenase | | | 35/36 | | | | | | | 41/42 |
| D | 4-Amino-1,8-naphthalimide | Apoptosis | PARP | | 41/42* | 41/42 | | | | | | | |
| | Sobuzoxane | Gene Regulation | Topo II | | 45* | | 45 | 47 | | | | | 47 |
| | SU 6656 | Phosphorylation | Src family kinases | | 41/42* | 41/42 | 45 | 45 | | | | | 46 |
| E | Retinoic acid | Transcription | RAR-alpha, beta | 39+ | | | | 40 | | | | | 39 |
| | 13-cis-retinoic acid | Transcription | RAR-alpha, beta | 45+ | | | 41/42 | 39/40 | 45 | | | | 46 |
| | TTNPB | Transcription | RAR-alpha, beta, gamma | 41/42+ | | | 41/42 | 41/42 | 39 | | | | 45 |

TABLE 8-continued

Phenotypic classification of edema-inducing compounds

| Phenotype class | Compound name | Pharmacological class | Selectivity | Type of edema | | | | | | | Cardiac phenotype | Lymph heart enlargement | Lethality |
|---|---|---|---|---|---|---|---|---|---|---|---|---|---|
| | | | | Cerebral | Periocular | Pericordial | Ventral | Proctodeal | Pronephric | Tail tip | | | |
| F | Genistein | Phosphorylation | Tyrosine kinase | | | | | | | | | | 41/42 |
| | IC 261 | Phosphorylation | CK-1 delta/epsilon | | 45 | 35/36 | | 41/42 | 41/42 | 35/36 | § | | 41/42 |
| | Tyrphostin AG 1478 | Phosphorylation | EGFR | | | 39 | 45 | | | | 45¶ | | 46 |
| | Tyrphostin AG 494 | Phosphorylation | EGFR | | | | | | | | § | | 40 |

*Periocular edema causing bulging eyes.
Bilateral periocular edemas causing narrow-set eyes.
+Cerebral edema extending dorso-anteriorly and displacing the eyes.
§ Heart tube tailed to loop.
¶The heart chambers were enlarged.
‡The edemas were also detected in the gut.
Numbers shown represent embryonic stages according to Nieuwkoop and Faber (NF).
Compound abbreviations:
7-Cyclo, 7-Cyclopentyl-5-(4-phenoxy)phenyl-7H-pyrrolo[2,3-d]pyrimidin-4-ylamine;
Naphthyridine, 7-Chloro-4-hydroxy-2-phenyl-1,8-naphthyridine.

TABLE 9

Vascular phenotypes resulting from small-molecule treatment of Xenopus embryos

A) Compounds affecting blood vessel development only

| Phenotype class | Compound name | Pharmacological class | Selectivity | ISV phenotype | VVN phenotype | PCV phenotype | Lymphatic phenotype | Embr. phen. |
|---|---|---|---|---|---|---|---|---|
| Defective vasculogenesis | Nocodazole | Cytoskeleton and ECM | beta-tubulin | impaired | hypoplastic | hypoplastic | n.a. | EDE |
| | Podophyllotoxin | Cytoskeleton and ECM | | impaired | hypoplastic | hypoplastic | n.a. | EDE |
| | 2-methoxyestradiol | Hormone | Estrogen | impaired | hypoplastic | hypoplastic | n.a. | EDE |
| | IC 261 | Phosphorylation | CK-1delta/epsilon | impaired | hypoplastic | hypoplastic | n.a. | EDE |
| | NSC 95397 | Phosphorylation | Cdc25 | impaired | hypoplastic | hypoplastic | n.a. | LET |
| | Tyrphostin AG 494 | Phosphorylation | EGFR | impaired | hypoplastic | hypoplastic | n.a. | EDE |
| | Meclotenamic acid sodium | Prostaglandin | COX/5-Lipoxygenase | impaired | hypoplastic | hypoplastic | n.a. | EDE |
| Defective angiogenesis | Retinoic acid | Apoptosis | | impaired | hypoplastic | nominal | n.a. | EDE |
| | Forskolin | Cyclic nucleotides | Adenylate cyclase | impaired | hypoplastic | normal | n.a. | EDE |
| | L-162,313 | Neurotransmission | AT1 | impaired | hypoplastic | normal | normal | LET |
| | Indirubin-3'-oxime | Phosphorylation | CDK | impaired | normal | normal | normal | LET |
| | SU 5416 | Phosphorylation | VEGFR PTK | impaired | hypoplastic | normal | n.a. | LET |
| Ectopic angiogenic sprouting | Calmidazolium chloride | Intracellular Calcium | Ca2+ ATPase | ectopic ISVs | hyperplastic | normal | n.a. | LET |
| | GW5074 | Phosphorylation | Raf 1 kinase | ectopic ISVs | dyspiastic | normal | n.a. | EDE |
| VVN hypoplasia | YC-1 | Cyclic nucleotides | Guanylyl cyclase | normal | hypoplastic | normal | normal | EDE |
| | Zardaverine | Cyclic nucleotides | PDE III/PDE IV | normal | hypoplastic | normal | n.a. | EDE |
| | MK-886 | Leukotriene | | normal | hypoplastic | normal | n.a. | LET |
| | Purvalanol A | Phosphorylation | CDK | normal | hypoplastic | normal | normal | LET |

B) Compounds affecting blood and lymph vessel formation

| Phenotype class | Compound name | Pharmacological class | Selectivity | ISV phenotype | VVN phenotype | PCV phenotype | ALS phenotype | ALH phenotype | PLV phenotype | Embr. phen. |
|---|---|---|---|---|---|---|---|---|---|---|
| Detective blood and lymph angiogenesis | Naphthyridine | Adenosine | A1 | stunted | hypoplastic | normal | stunted | dysplastic | hypoplastic | EDE |
| | 7-Cyclo | Phosphorylation | Ick | stunted | normal | normal | impaired | impaired | hypoplastic | EDE |
| | SP600125 | Phosphorylation | c-JNK | stunted | dyspiastic | normal | impaired | impaired | impaired | LET |
| VVN hyperplasia and defective lymph angiogenesis | 1,3-Diethyl-8-phenylxanthine | Adenosine | A1 | normal | hyperplastic | normal | stunted | stunted | hypoplastic | EDE |
| | 4-Amino-1,8-naphthalimide | Apoptosis | PARP | normal | hyperplastic | normal | impaired | stunted | hypoplastic | EDE |
| | Genistein | Phosphorylation | Tyrosine kinase | stunted | hyperplastic | normal | impaired | impaired | impaired | EDE |

TABLE 9-continued

Vascular phenotypes resulting from small-molecule treatment of Xenopus embryos

C) Compounds affecting lymph vessel formation only

| Phenotype class | Compound name | Pharmacological class | Selectivity | Blood vessel phenotype | ALS phenotype | ALH phenotype | PLV phenotype | Embr. phen. |
|---|---|---|---|---|---|---|---|---|
| Defective lymph angiogenesis | Felodipine | Ca2+ Channel | L-type | normal | normal | dysplastic | normal | EDE |
| | Sobuzoxane | Gene regulation | Topo II | normal | dysplastic | dysplastic | hypoplastic | EDE |
| | Nicardipine hydrochloride | Ca2+ Channel | L-type | normal | dysplastic | dysplastic | hypoplastic | EDE |
| | SU 6656 | Phosphorylation | Src family kinase | normal | stunted | dysplastic | hypoplastic | EDE |
| | Dequalinium dichloride | K+ channel | | normal | stunted | stunted | hypoplastic | EDE |
| | GW2974 | Phosphorylation | EGER/ ErbB2-2 | normal | impaired | stunted | hypoplastic | EDE |
| | Mevastatin | Antibiotic | Ras, Rho | normal | impaired | impaired | hypoplastic | EDE |
| | SU 4312 | Phosphorylation | KDR | normal | impaired | impaired | hypoplastic | EDE |

Abbreviations:
ALH, anterior lymph heart;
ALS, anterior lymph sac;
EDE, edema phenotype;
ISV, intersomitic vessels;
LET, lethal before stage 48;
n.a., not applicable;
PCV, posterior cardinal vein;
Phen, phenotype;
PLV, posterior lymph vessels;
VVN, vitelline vein network.
Compound abbreviations:
7-Cyclo, 7-Cyclopentyl-5-(4-phenoxy)phenyl-7H-pyrrolo[2,3-d]pyrimidin-4-ylamine;
Naphthyridine, 7-Chloro-4-hydroxy-2-phenyl-1,3-naphthyridine.

TABLE 10

Comparison between the in vivo and in vitro activities of small-molecule compounds

| Phenotype class in vivo | Compound name | HUVEC proliferation | HUVEC tube formation | LEC proliferation | LEC tube formation |
|---|---|---|---|---|---|
| A) Compounds affecting in vivo blood vessel development only | | | | | |
| Defective vasculogenesis | Nocodazole | − | − − | − | − − |
| | Podophyllotoxin | − | − − | − | − − |
| | 2-methoxyestradiol | O | − − | − | − |
| | IC 261 | O | − | − | − |
| | Tyrphostin AG 494 | O | O | O | − |
| Defective angiogenesis | Retinoic acid | + | − | + | − |
| | L-162, 313 | + | − | O | − |
| | Indirubin-3′-oxime | − | − | O | O |
| | SU 5416 | O | O | O | − |
| Ectopic angiogenic sprouting | GW5074 | O | O | + | − |
| VVN hypoplasia | MK-886 | + | − | O | − |
| B) Compounds affecting in vivo blood and lymph vessel formation | | | | | |
| Defective blood and lymphangiogenesis | Naphthyridine | − − | − | − − | − |
| | 7-Cyclo | O | − − | O | − − |
| | SP600125 | O | O | O | − |
| VVN hyperplasia and defective lymphangiogenesis | 1,3- Diethyl-8-phenylxanthine | O | + | O | O |
| | 4-Amino-1,8-naphthalimide | + | O | O | − |
| | Genistein | O | − | O | − |

TABLE 10-continued

Comparison between the in vivo and in vitro activities of small-molecule compounds

| Phenotype class in vivo | Compound name | HUVEC proliferation | HUVEC tube formation | LEC proliferation | LEC tube formation |
|---|---|---|---|---|---|
| C) Compounds affecting in vivo lymph vessel formation only | | | | | |
| Defective lymphangiogenesis | Felodipine | O | – | O | O |
| | Sobuzoxane | + | O | + | O |
| | Nicardipine hydrochloride | O | O | O | O |
| | GW2974 | + | – | + | – |
| | SU 4312 | + | O | O | O |
| D) Compounds without vascular detects in vivo | | | | | |
| — | Cyclosporin A | O | O | O | O |
| | MRS 1845 | + | O | O | – |
| | L-687, 384 hydrochloride | + | – | O | – |

Scoring system for in vitro assays:
O, inactive or marginal effects (85-115% of control);
–, moderate inhibition (50-85% of control);
– –, strong inhibition (<50% of control);
+, moderate promotion (>115-150% of control).
Abbreviations:
HUVEC, human umbilical vein endothelial cell;
LEG, lymphatic endothelial cell;
VVN, vitelline vein network.
Compound abbreviations:
7-Cyclo, 7-Cyclopentyl-5-(4-pherioxy)phenyl-7H-pyrrolo[2,3-d]pyrimidin-4-ylamine;
Naphthyridine, 7-chloro-4-hydroxy-2-phenyl-1,8-naphthyridine.

What is claimed is:

1. A method for in vivo screening to identify compounds that modulate fluid homeostasis having an underlying pathophysiological function in the cardiovascular, lymphatic, and excretory systems comprising: a) treating a plurality of amphibians with a plurality of agents; b) identifying an amphibian from the plurality of amphibians wherein the treatment causes edema in the amphibian; and c) determining the anatomical pattern of edema formation in the identified amphibian.

2. The method of claim 1, wherein the plurality of amphibians are treated by including the plurality of agents in the culture media containing the plurality of amphibians.

3. The method of claim 2, wherein the plurality of agents are dissolved in the culture media containing the plurality of amphibians.

4. The method of claim 1, wherein the method is performed in a multi-well format.

5. The method of claim 1, wherein the plurality of amphibians are a plurality of embryos, tadpoles, or adults.

6. The method of claim 1, wherein the plurality of amphibians are from the subclass Lissamphibia.

7. The method of claim 6, wherein the plurality of amphibians are frogs, toads, newts, salamanders, mudpuppies, or caecilians.

8. The method of claim 1, wherein the plurality of amphibians are from the genus *Xenopus*.

9. The method of claim 8, wherein the plurality of amphibians are from the species *Xenopus laevis* or *Xenopus tropicalis*.

10. The method of claim 1, wherein the plurality of agents are independently small molecules, drugs, antibodies, peptides, secreted proteins, nucleic acids, antisense RNA molecules, ribozymes, RNA interference nucleotide sequences, antisense oligomers, or morpholino oligonucleotides.

11. The method of claim 1, wherein the edema is caused by an activity in the vascular, lymphatic, cardiac, or excretory system of the identified amphibian.

12. The method of claim 1, further comprising the step of identifying the target tissue or organ of the agent responsible for the edema in the identified amphibian.

13. The method of claim 1, wherein the anatomical pattern of edema formation in the identified amphibian is cerebral, periocular, pericardial, ventral, proctodeal, pronephric, or tail tip.

14. The method of claim 1, wherein the anatomical pattern of edema formation in the identified amphibian is a cardiac phenotype or a lymph-heart enlargement.

15. The method of claim 1, wherein the method further comprises a secondary screen.

16. The method of claim 15, wherein the secondary screen is performed by in situ hybridization.

17. The method of claim 16, wherein the in situ hybridization is performed manually, semi-automated or fully automated.

18. The method of claim 15, wherein the secondary screen is performed by immunohistochemistry.

19. The method of claim 18, wherein the immunohistochemistry is performed manually, semi-automated or fully automated.

20. The method of claim 1, wherein the method further comprises the step of d) identifying the agent causing the edema in the amphibian.

21. The method of claim 1, wherein the method further comprises the step of d) identifying a pathway that mediates lymphatic and/or vascular development in the identified amphibian.

22. The method of claim 21, wherein the pathway is a vascular endothelial growth factor (VEGF) pathway.

23. The method of claim 22, wherein the pathway is targeted by an adenosine receptor antagonist.

* * * * *